United States Patent
Mihai

(10) Patent No.: US 10,430,552 B2
(45) Date of Patent: Oct. 1, 2019

(54) DISTRIBUTED TELEMEDICINE SYSTEM AND METHOD

(71) Applicant: Dan M. Mihai, Hanover Park, IL (US)

(72) Inventor: Dan M. Mihai, Hanover Park, IL (US)

( * ) Notice: Subject to any disclaimer, the term of this patent is extended or adjusted under 35 U.S.C. 154(b) by 314 days.

(21) Appl. No.: 15/396,421

(22) Filed: Dec. 31, 2016

(65) Prior Publication Data

US 2017/0193182 A1 Jul. 6, 2017

Related U.S. Application Data

(60) Provisional application No. 62/273,811, filed on Dec. 31, 2015.

(51) Int. Cl.
*G06F 19/00* (2018.01)
*G16H 80/00* (2018.01)
*A61B 5/00* (2006.01)

(52) U.S. Cl.
CPC ........ *G06F 19/3418* (2013.01); *A61B 5/0022* (2013.01); *G16H 80/00* (2018.01); *A61B 5/002* (2013.01)

(58) Field of Classification Search
USPC .......................................................... 705/2
See application file for complete search history.

(56) References Cited

U.S. PATENT DOCUMENTS

| | | | | |
|---|---|---|---|---|
| 7,027,871 B2* | 4/2006 | Burnes | ............... | A61B 5/0031 607/60 |
| 8,170,887 B2* | 5/2012 | Rosenfeld | ............. | G16H 50/20 705/2 |
| 2007/0271122 A1* | 11/2007 | Zaleski | ............... | A61B 5/1113 705/3 |
| 2008/0004904 A1* | 1/2008 | Tran | ..................... | A61B 5/0006 705/2 |
| 2009/0105567 A1* | 4/2009 | Smith | ..................... | H04W 4/70 600/323 |
| 2010/0094098 A1* | 4/2010 | Smith | ................. | A61B 5/0836 600/300 |
| 2011/0246235 A1* | 10/2011 | Powell | ................... | G06Q 10/10 705/3 |
| 2012/0155387 A1* | 6/2012 | Simons | .............. | G06F 19/3418 370/328 |

(Continued)

*Primary Examiner* — Jason C Olson
(74) *Attorney, Agent, or Firm* — Michael D. Eisenberg

(57) ABSTRACT

A vital-signs enhanced telemedicine system and method allowing a plurality of medical teams assisting a plurality of patients to interact with and get assistance from a plurality of remote physicians via a plurality of audio, video, and vital signs transmissions and interactive remoting sessions including alarms, analysis, recording, and live playback capabilities.

The system includes patient monitoring devices generating streaming vital signs, alarms and alerts (monitoring); aggregators generating streaming audio, video, and GPS for transmission in combination with monitoring received (session) and receiving sessions and instructions from gateways for local display; gateways maintaining concurrent sessions between aggregators and dashboards, receiving sessions from aggregators for transmission to dashboards, and simultaneously receiving sessions from dashboards for transmission, with instructions, to aggregators and to other session dashboards; and dashboards generating and streaming session to gateways while displaying received session data.

120 Claims, 10 Drawing Sheets

(56) References Cited

U.S. PATENT DOCUMENTS

| | | | | |
|---|---|---|---|---|
| 2013/0162433 A1* | 6/2013 | Muhsin | ................ | G08B 25/008 340/573.1 |
| 2013/0267873 A1* | 10/2013 | Fuchs | ...................... | H04N 7/18 600/595 |
| 2013/0275152 A1* | 10/2013 | Moore | ................... | G06Q 10/10 705/3 |
| 2014/0018779 A1* | 1/2014 | Worrell | ............... | G06F 19/3418 606/1 |
| 2014/0235293 A1* | 8/2014 | Sheldon | ............... | A61B 5/0205 455/556.1 |
| 2014/0316792 A1* | 10/2014 | Siddiqui | ............. | G06F 19/3418 705/2 |
| 2014/0368601 A1* | 12/2014 | deCharms | ............ | H04W 4/021 348/14.02 |
| 2018/0122506 A1* | 5/2018 | Grantcharov | ....... | G06F 19/3481 |

* cited by examiner

DISTRIBUTED TELEMEDICINE SYSTEM AND METHOD

TECHNICAL FIELD

Embodiments of the present invention relate to a distributed telemedicine system and method providing an interactive telepresence combined with real time, streaming vital signs connectivity between a plurality of medical professionals in either fixed or mobile settings and a plurality of patients and/or physician assistants in either fixed or mobile settings at remote sites.

BACKGROUND

Interactive telemedicine systems with telepresence have traditionally been available in stationary settings, predicated on the availability of a reliable, high bandwidth communication infrastructure between the locations of the physician and the patient, such as a rural clinic, ambulatory center, or assisted living facility, and vital-signs based telemedicine systems have traditionally been used for home monitoring of post-operative patients, preventative medicine, and for communications of patient self-administered tests where a reliable, high bandwidth communication infrastructure is not necessarily available and where the connectivity is of store-and-forward (non-interactive) nature, the remote comprising primarily of trended, incremental snapshots of streaming vital signs and/or a limited number of pre-recorded audio, video, and/or vital sign waveform snippets.

Currently available telemedicine systems are of limited value in mobile applications such as emergency medical assistance at the site of an accident or during patient transport to a medical facility, where telepresence is either not available or is not interactive, and/or streaming vital signs transmission is limited to selective snapshots taken at the initiative of an Emergency Medical Technician or physician assistant, therefore limiting the clinical effectiveness of the assistance provided by the remote physician.

Since the level and type of remote assistance available in such emergency situations is typically limited to the qualifications of the medical staff present within the medical facility where the fixed telemedicine terminal is located, hospitals are required to ensure adequate staffing coverage for all possible trauma conditions not knowing ahead of time the types of trauma present at the accident site.

Moreover, since most telemedicine systems are structured in a point-to-point fashion, multiple physician collaborations are limited to just the personnel available at the location where the fixed telemedicine terminal is installed.

Lastly, current telemedicine systems offer neither live pause, rewind, and play back capabilities which might be useful in real time remote review, assessment, and diagnosis of clinical conditions, events, and/or triggers such as arrhythmias, temporary drops in blood pressure, respiratory blockages, etc. for a more effective remote assistance of patients with critical or life threatening conditions, nor full session archiving and playback of audio, video, and streaming vital signs which could be useful for post case review related to insurance claims, liability litigation, and training or educational applications.

There is thus a widely-recognized need for, and it would be highly helpful to the advancement of the current standard of critical care to have, a telemedicine system which is devoid of all the above limitations.

SUMMARY

A distributed telemedicine system for medical remote assistance applications, the telemedicine system comprising: one or more patient monitoring devices, the patient monitoring device comprising: one or more vital signs sensors configured for physical attachment to a patient; a first communication system; a first processor configured to receive vital signs information from the one or more sensors, generate streaming vital signs based on the information and transmit at least a first portion of the streaming vital signs to an aggregator via the first communication system; and a first screen configured to display a representation of at least a second portion of the streaming vital signs; one or more aggregators, the aggregator comprising: one or more audio and video sensors; a second communication system; a third communication system; a fourth communication system; a fifth communication system; a second processor configured to receive site audio and video from the audio and video sensors and streaming vital signs from the one or more patient monitoring devices via the second communication system, transmit at least a third portion of the streaming vital signs to a first gateway via the third communication system, transmit the site audio and video to a second gateway via the fourth communication system and receive backchannel audio data from a third gateway via the fifth communication system; a first application executed on the second processor, the application configured to detect the presence of the first communication system and establish a communication link between the first and second communication system, detect the presence of the sixth communication system and establish a communication link between the third and sixth communication system, detect the presence of the seventh communication system and establish a communication link between the fourth and seventh communication system, detect the presence of the eighth communication system and establish a communication link between the fifth and eighth communication system; a second screen configured to display an aggregated representation of at least a fourth portion of the streaming vital signs together with the site video and session controls; one or more first audio reproduction devices configured to reproduce the site audio combined with the backchannel audio as audible sounds; one or more gateways, the gateway comprising: a sixth communication system; a seventh communication system; an eighth communication system; a ninth communication system; a third processor configured to receive site audio and video from a plurality of aggregators over the seventh communication system, receive streaming vital signs from a plurality of aggregators over the sixth communication system, send the site audio and video combined with the streaming vital signs to a plurality of dashboards over the ninth communication system, receive backchannel audio from a plurality of dashboards over the ninth communication system, and transmit backchannel audio to a plurality of aggregators over the eighth communication system; a third screen configured to display session status, statistics, and configuration controls; one or more dashboards, the dashboard comprising: a tenth communication system; an audio sensor; a fourth processor configured to receive site audio and video and streaming vital signs data from a gateway over the tenth communication system and to send audio backchannel data to a gateway over the tenth communication system; one or more audio reproduction devices configured to reproduce the site audio data received as audible sounds; a second application executed on the fourth processor, the application configured to detect the presence of the ninth communication system and establish a communication link between the ninth and tenth communication system; a fourth screen configured to display an aggregated representation of at least a fifth portion of the streaming vital signs combined with a representation of the site video and session controls; and one or more second audio reproduction devices configured to reproduce the site audio received as audible sounds.

The telemedicine system, wherein the third and fourth communication systems are the same.

The telemedicine system, wherein the fourth and fifth communication systems are the same.

The telemedicine system, wherein the sixth and seventh communication systems are the same.

The telemedicine system, wherein the seventh and eighth communication systems are the same.

The telemedicine system, wherein the first and second gateways are the same.

The telemedicine system, wherein the second and third gateways are the same.

The telemedicine system, wherein the first and second portions of the streaming vital signs data are the same.

The telemedicine system, wherein the second and third portions of the streaming vital signs data are the same.

The telemedicine system, wherein the third and fourth portions of the streaming vital signs data are the same.

The telemedicine system, wherein the fourth and fifth portions of the streaming vital signs data are the same.

The telemedicine system, wherein at least a portion of either communication system includes a fixed network over wire, fiber optic cables, or power line in either point-to-point, shared media, bus, ring, backbone, star, backhaul, ad-hoc, mesh topology configuration or any combination thereof.

The telemedicine system, wherein at least a portion of either communication system includes a wireless network, including, without limitation, Bluetooth, Bluetooth Low Energy (BLE), Ultra Wide Band (UWB), Wireless Fidelity (Wi-Fi), radio, satellite, microwave, laser, infrared, Zig-bee, Z-Wave, or cellular such as Time Division Multiple Access (TDMA), Code Division Multiple Access (CDMA), Global System for Mobile Communications (GSM), Long-Term Evolution (LTE), Extended Long-Term Evolution (XLTE), etc., in either point-to-point, shared media, bus, ring, backbone, star, backhaul, ad-hoc, mesh topology configuration or any combination thereof.

The telemedicine system, wherein the patient monitor and the aggregator are the same.

The telemedicine system, wherein either of the patient monitoring devices are portable.

The telemedicine system, wherein either of the aggregators are portable.

The telemedicine system, wherein either of the gateways are portable.

The telemedicine system, wherein either of the dashboards are portable.

The telemedicine system, wherein either of the screens are touch-enabled.

The telemedicine system, wherein either of the gateways are cloud-based virtual server instances.

The telemedicine system, wherein either of the gateways are physical server instances, either on-site, collocated or cloud-based.

The telemedicine system, wherein either of the gateways are a server cluster system capable of redirecting, recording, or modifying communication between transmitters and receivers with manual or automatic computing resource scaling including, but not limited to, Amazon Elastic Compute Cloud (EC2) instances, Microsoft Azure instances, Google Compute Engines, Google Autoscaler, etc.

The telemedicine system, wherein at least a portion of the data transmission over either of the communication systems uses as baseline protocols either Transmission Control Protocol/Internet Protocol (TCP/IP), User gram Protocol (UDP), Internet Control Message Protocol (ICMP), or their FastPath Stack successor in any combination thereof.

The telemedicine system, wherein at least a portion of the data transmission over either of the communication systems is secured with an encryption method including but not limited to the Secure Sockets Layer (SSL) protocol, Transport Layer Security (TLS), etc.

The telemedicine system, wherein at least a portion of the audio and/or video transmission over either of the communication systems uses the World Wide Web Consortium's (W3C) Web Real-Time Communication (WebRTC) protocol.

The telemedicine system, wherein at least a portion of the streaming vital signs data transmission over either of the communication systems uses the Internet Engineering Task Force's (IETF) WebSocket protocol.

The telemedicine system, wherein access to either of the communication systems is protected with either single or multiple factor authentication schemes consisting of a user ID/password, a digital certificate such as the Public Key Infrastructure (PKI)-based X.509 certificate, a biometric reading such as the image of a fingerprint, a retinal scan, facial recognition, or any combination thereof.

The telemedicine system, wherein the audio, video, and streaming vital signs data transmitted over either of the communication systems are partitioned in fixed size packets each representing a time interval configurable to any value between 20 milliseconds and 2 seconds.

The telemedicine system, wherein either of the communication systems transmit new packets of either audio, video, or vital signs data at constant time intervals, programmable between 40 to 960 milliseconds.

The telemedicine system, wherein either of the data packets transmitted over either of the communication systems is structured according to JavaScript Object Notation (JSON) specification.

The telemedicine system, wherein either of the packets transmitted over either of the communication systems uses a lossless compression algorithm like Huffman Coding, arithmetic coding, context-free weighing (CTW), Run-Length Limited (RLL), Lempel-Ziv 77 (LZ77), Lempel-Ziv 78 (LZW78), Lempel-Ziv-Storer-Symanski (LZSS), Lempel-Ziv-Markov (LZM), Lempel-Ziv-Welch (LZW), Burrows-Wheeler Transform (BZT), Brotti, Zopfli, Sequitur, Prediction by Partial Matching (PPM) etc. or any component, combination, or derivative thereof, such as zip, gzip, pkzip, arc, rar, etc.

The telemedicine system, wherein the streaming vital signs include, without limitation, waveforms such as 3, 5, 7, or 12-lead electrocardiogram (ECG), respiration, invasive blood pressure, and temperature; trending numeric parameters such as blood oxygen saturation level (SPO2), End-Tidal CO2 (EtCO2), heart rate, respiration rate, non-invasive blood pressure, temperature, streaming ultrasound images, streaming endoscopic images, stethoscope ascultation patterns, etc.; patient monitor generated alarms such as ventricular fibrillation, etc. and patient monitor generated alerts such as blood pressure lower than a preset alert limit, etc.

The telemedicine system, wherein either of the patient monitoring devices is a monitor-defibrillator.

The telemedicine system, wherein the gateway also comprises a first persistent memory device and a third application executed on the third processor, the application configured to capture and store within the first persistent memory device a timestamped copy of all the site audio, video, backchannel audio, and streaming vital signs passing through the gateway.

The telemedicine system, wherein the gateway further comprises a fourth application executed on the third processor, the application configured to respond to pause, play back, rewind, and fast forward commands received over the ninth communication system, read the timestamped site audio, video, backchannel audio, and streaming vital signs stored in the first persistent memory device, apply a controlled time offset for each such function requested, and send it to one or more dashboards over the ninth communication system to provide the requested pause, play back, rewind, and fast forward functionality within the dashboard's fourth screen, and the dashboard further comprises a fifth application executed on the fourth processor, the application configured to read user input and transmit pause, play back, rewind, and fast forward commands to the gateway's fourth application via the tenth communication system.

The telemedicine system, wherein the gateway's third application is also programmed to capture and store within the first persistent memory device a timestamped copy of all the site audio, video, backchannel audio, textual chat messages, and streaming vital signs received by the gateway even if either the ninth or the tenth communication systems are inoperative, to be made available under the request and control of the dashboard by the gateway's fourth application when both the ninth and the tenth communication systems resume their operation and reconnect.

The telemedicine system, wherein the aggregator also comprises a second persistent memory device and a fifth application executed on the second processor, the application configured to capture and store a persistent, timestamped copy of all the site audio, video, and streaming vital signs received by the aggregator when either the third, fourth, or fifth communication system is inoperative, and the aggregator's second application is also configured to send the stored (catch-up) in a catch-up mode, until all the catch-up is exhausted, to the one or more gateways when all of the third, fourth, and fifth communication systems resume their operation and reconnect, and the gateway's third application is also configured to receive the timestamped catch-up from the gateway through the sixth, seventh, and eighth communication system respectively, insert and store the catch-up, until all the catch-up is exhausted, in its correct timestamp order within the first persistent memory device simultaneously with it storing in the same first persistent memory a timestamped copy of all the current site audio, video, backchannel audio, and streaming vital signs passing through the gateway.

The telemedicine system, wherein the gateway also comprises a sixth application executed on the third processor, the application configured to group a plurality of gateway login accounts and a plurality of dashboard login accounts into Virtual Medical Groups (VMG) and only allow the communication of site audio, video, backchannel audio, and vital signs between the gateways and dashboards where the users logged in belong to the same VMG, the gateway's third screen also configured to allow a system administrator to create, modify, and remove VMGs through the allocation and deallocation of individual gateway and dashboard login accounts to VMGs, in either an exclusive or a shared fashion.

The telemedicine system, wherein the aggregator also comprises a first GPS location sensor and seventh application executed on the second processor, the application configured to read its GPS position from its first GPS sensor, initiate an assistance request combined with its GPS position indicating the type of expertise sought and transmit such assistance request to one or more gateways via the fifth communication system, wherein the gateway also comprises an eight application executed on the third processor which receives such assistance requests and forwards them to one or more of the dashboards whose logged in users belong to the same VMG as the user logged into the requesting gateway and according to a preprogrammed priority based on their type of expertise registered with the system, and wherein the dashboard also comprises a ninth application executed on the fourth processor, the application programmed to display the assistance request on a geolocation map using the GPS information embedded in the assistance request, wait for the logged in user to confirm, and if confirmed within a programmed window of time, initiate an end-to-end audio, video, and streaming vital signs session between the dashboard and the requesting aggregator through the connecting gateway. If the user does not confirm the assistance request within the preprogrammed time, the gateway's eighth application executed on the third processor forwards the assistance request, according to a preprogrammed escalation logic and based on their type of expertise registered with the system, to another dashboard whose logged in user belongs to the same VMG as the requesting gateway's logged in user. If no dashboard with a logged in user belonging to the same VMG as the requesting gateway's logged in user exists at that time, the gateway's eighth application executed on the third processor is programmed to hail the next recipient according to a programmed escalation logic and based on their type of expertise registered with the system, through an external channel including but not limited to, a SMS message over a cellular network, an e-mail, a text-to-speech voice message over a cellular or traditional phone network, etc. The dashboard's ninth application executed on the fourth processor is also programmed to display the pending assistance request on a geolocation map using the GPS information embedded in the assistance request when the user hailed though an external channel logs into the dashboard, wait for the logged in user to confirm, and if confirmed within a programmed window of time, initiate an end-to-end audio, video, and streaming vital signs session between the dashboard and the requesting aggregator through the connecting gateway.

The telemedicine system, wherein the dashboard's ninth application executed on the fourth processor is also programmed to allow a dashboard user providing assistance to an aggregator user through an active end-to-end session to send a secondary assistance request based on the same or different requested second skill set to another nominated or generic user from the same VNG through the tenth communication system, and the eighth application executed on the third processor is also programmed to receive such a secondary assistance request and dispatch it to the nominated user or to the next qualified user from the same VMG and according to its programmed escalation logic. The gateway's ninth application executed on the fourth processor is further programmed to display the secondary user's pending assistance request on a geolocation map using the GPS information embedded in the original assistance request, wait for the secondary user to confirm, and if confirmed within a programmed window of time, initiate a secondary dashboard session with the same gateway user as the dashboard user placing the secondary assistance request. The fourth screen is also configured to render, when the dashboard is in such a secondary assistance mode, a replica of the primary session's streaming vital signs and site video;

the second audio reproduction device is also configured to reproduce, when the dashboard is in such a secondary assistance mode, a replica of the site audio combined with the composite backchannel audio originating from all session dashboards.

The telemedicine system, wherein the eighth application executed on the gateway's third processor is also programmed to combine all backchannel audio originating from the primary and all secondary dashboard users providing assistance to the same gateway user, and send the combined audio backchannel forward to the aggregator and back to the primary and all secondary dashboards connected to the same gateway session.

The telemedicine system, wherein the third, fourth, and fifth communication systems are the same, the sixth, seventh, and eighth communication systems are the same, the first, second, and third gateways are the same, and the site audio, video, and streaming vital signs are partitioned in packets each representing such originating within the same 40 to 960 milliseconds time interval, and whereby all such packets are further combined in a single composite packet that encompasses all site audio, video, and streaming vital signs originating within the said time interval.

The telemedicine system, wherein the composite data packet (payload) is further compressed, and whereby the compressed data packet may also include derived information used to detect the tampering and/or corruption of the payload including, but not limited to, an electronic signature performed with the aid of symmetric or asymmetric key scheme, a hash, a checksum, a digital watermark, a cryptographic timestamp, etc.

The telemedicine system, wherein the gateway also comprises a tenth application executed on the third processor, the application configured to take a snapshot of ECG from the gateway's first persistent memory device, perform a 12-Lead analysis through a third party analysis module including, but not limited to, GE-Marquette 12SL, Glasgow 12-Lead ECG Analysis, ZOLL Inovise, Philips EASI, etc., generate a 12 Lead ECG analysis report, and send such report to the dashboard over the ninth communication system, and the dashboard also comprises an eleventh application executed on the fourth processor, the application configured to send a 12 Lead ECG analysis request to the gateway over the tenth communication system, receive the 12 Lead analysis report, and the dashboard's fourth screen is also configured to render the said 12 Lead Analysis report.

The telemedicine system, wherein the gateway's tenth application executed on the third processor is also configured to archive the generated 12 Lead ECG analysis report into the gateway's first persistent memory device, the gateway's fourth application executed on the third processor is also programmed to respond to a retrieval command of a previously generated 12 Lead ECG analysis report, and send such report to the dashboard over the ninth communication system, the dashboard's eleventh application executed on the fourth processor is also configured to send a retrieval command for a previously generated 12 Lead ECG analysis to the gateway over the tenth communication system, receive the said 12 Lead analysis report from the gateway over the tenth communication system, and the dashboard's fourth screen is also configured to render the previously generated 12 Lead Analysis report received from the gateway.

The telemedicine system, wherein the 12 Lead ECG analysis is substituted with any derivative calculation, analysis, alarm, or alert executed across any number of streaming vital signs, including but not limited to, ECG, temperature, invasive blood pressure, and respiration waveforms, trending numerical parameters such as EtCO2, SPO2, temperature, streaming ultrasound or endoscopic images, auscultation waveforms, respiration rate, heart rate, non-invasive blood pressure, etc. and/or including patient monitor generated alarms and alerts.

The telemedicine system, wherein the gateway's tenth application executed on the third processor is also configured to use machine learning algorithms included but not limited to, neural networks, fuzzy logic, artificial intelligence, etc. based on previously stored streaming vital signs received from at least a portion of all the other patients' vital signs received and stored in its first persistent memory device to improve the accuracy of at least a portion of all of its derivative calculations, analyses, alarms, or alerts.

The telemedicine system, wherein the gateway's tenth application executed on the third processor is also configured to use for its machine learning algorithms externally provided historical streaming vital signs data either preloaded into the gateway's first persistent memory device or downloaded from an external data provider over its eighth communication system, or a combination of internally stored and externally accessed such.

The telemedicine system, wherein the gateway's tenth application executed on the third processor is also configured to archive a time stamped textual and/or voice recording annotation event into the gateway's first persistent memory device alongside the currently recorded site audio, video, and streaming vital signs, the gateway's fourth application executed on the third processor is also programmed to receive a current annotation event for storage and respond to a voice or textual retrieval command of a previously stored annotation event, generate a search specification based on an algorithm including, but not limited to, voice recognition, text to speech, neural networks, fuzzy logic, artificial intelligence, Boolean, binary tree, etc., search based on the generated search specification and its associated algorithm, locate, and send such previously stored annotation event together with all the previously stored backchannel audio, site audio, video, and streaming vital signs in a configurable time window surrounding the time stamp of the first annotation event match to the dashboard over the ninth communication system, the dashboard's eleventh application executed on the fourth processor is also configured to capture a new textual or voice recorded annotation event and send it to the gateway over the tenth communication system, and to capture a textual or voice search request for a previously stored annotation event and send it to the gateway over the tenth communication system, receive the said previously stored annotation event together with all the previously stored site audio, video, and streaming vital signs from its configurable time window from the gateway over the tenth communication system, and the dashboard's fourth screen is also configured to render the received annotation event synchronized and together with all the received site audio, video, and streaming vital signs from its configurable time window.

The telemedicine system, wherein the gateway's fourth application executed on the third processor is also programmed to apply its generated search criteria to the site and/or backchannel voice recorded in the gateway's first persistent storage device and send such previously stored backchannel audio, site audio, video, and streaming vital signs in a configurable time window surrounding the time stamp of the first audio match to the dashboard over the ninth communication system, the dashboard's eleventh application executed on the fourth processor is also configured to the dashboard's eleventh application executed on the fourth processor is also configured to capture a search request to be executed over the site and/or backchannel voice recorded in the gateway's first persistent storage device, and send it to the gateway over its tenth communication system, receive the said previously stored backchannel audio, site audio, video, and streaming vital signs from its configurable time window from the gateway over the tenth communication system, and the dashboard's fourth screen is also configured to render the received backchannel audio, site audio, video, and streaming vital signs from its configurable time window.

The telemedicine system, wherein the gateway's fourth application executed on the third processor is also programmed to send either the first, last, next, or previous such search's match to the dashboard over the ninth communication system in response to a request received from it, and the dashboard's eleventh application executed on the fourth processor is also configured to request the first, last, next, or previous such search's match.

The telemedicine system, wherein the gateway also comprises a twelfth application executed on the third processor, the application configured to receive a textual or voice search request from an aggregator over the eighth communication system, generate a search specification based on an algorithm including, but not limited to, voice recognition, text to speech, neural networks, fuzzy logic, artificial intelligence, Boolean, binary tree, etc., search based on the generated search specification and its associated algorithm, locate and retrieve a previously stored procedural guidance including, but not limited to, text, hypertext, annotated text, structured text, images, audio, video, or any combination thereof, and send the first match of such previously stored procedural guidance to the requesting aggregator over the eighth communication system, the aggregator also comprises a thirteenth application executed on the second processor, the application configured to capture a textual or voice search request for a procedural guidance and send it to the gateway over the fifth communication system, and the aggregator's second screen is further configured to render the received procedural guidance in its appropriate representation, whether text, images, audio, video, or any combination thereof, either as standalone or as an overlay.

The telemedicine system, wherein the gateway's twelfth application executed on the third processor is also configured to search and retrieve procedural guidance data downloaded from an external data provider over its ninth communication system, or a combination of internally stored and externally accessed procedural guidance data.

The telemedicine system, wherein the gateway's twelfth application executed on the third processor is also programmed to send to the aggregator either the first, last, next, or previous such search's match over the eighth communication system in response to a request received from it, and the aggregator's thirteenth application executed on the second processor is also configured to request the first, last, next, or previous such search's match.

The telemedicine system, wherein the gateway also comprises a portable augmented reality display including, but not limited to, headset, goggle, retinal scanning device, smart glass eyewear such as Google Glass, Microsoft HoloLens, Sony SmartGlass, etc., programmed to display the said procedural guidance data received from the gateway over the fifth communication system.

The telemedicine system, wherein the gateway also comprises a haptic feedback device, the gateway's second screen is also configured to trigger and actuate the haptic feedback device in response to a selection of preprogrammed biological conditions detected in the streaming vital signs being displayed including, but not limited to, heart beats, respiratory cycles, preprogrammed biological parameter limits such as temperature, EtCO2, SPO2, invasive blood pressure being reached, etc., and when patient monitor-generated alarm or alert conditions are being detected as part of the streaming vital signs being displayed.

The telemedicine system, wherein the dashboard also comprises a haptic feedback device, the dashboard's fourth screen is also configured to trigger and actuate the haptic feedback device in in response to a selection of preprogrammed biological conditions detected in the streaming vital signs being displayed including, but not limited to, heart beats, respiratory cycles, preprogrammed biological parameter limits such as temperature, EtCO2, SPO2, invasive blood pressure being reached, etc., and when patient monitor-generated alarm or alert conditions are being detected as part of the streaming vital signs being displayed.

The telemedicine system, wherein the haptic feedback pattern is programmed to be unique for each group or individual type of biological conditions, alarms, or alert triggers.

The telemedicine system, wherein the dashboard also comprises a video sensor and its fourth processor is also configured to receive streaming video from the video sensor and transmit it as backchannel video to a gateway over the tenth communication system; the gateway's third processor is also configured to receive backchannel video from a dashboard over the ninth communication system, then transmit the received backchannel video to an aggregator over the seventh communication system and simultaneously to all other dashboards connected to the same active session over the ninth communication system; the dashboard's fourth processor is also configured to receive backchannel video originating from all the other dashboards connected to the same active session and its fourth display is also configured to render the backchannel video originating from all the other session dashboards in independent areas, each identifying its originating dashboard user; the aggregator's second processor is also configured to receive backchannel video from a gateway over its fifth communication system and its second display is also configured to render the backchannel video originating from all session dashboards in independent areas, each identifying its originating dashboard user.

The telemedicine system, wherein the gateway's third application executed on the third processor is further configured to capture and store within the first persistent memory device a timestamped copy of all or predesignated portions of the backchannel video data passing through the gateway.

The telemedicine system, wherein the dashboard also comprises a second GPS location sensor and its fourth processor is also configured to read its GPS location from the GPS sensor and transmit it as GPS alongside backchannel audio to a gateway over the tenth communication system; the gateway's third processor is also configured to receive GPS location alongside backchannel audio from a dashboard over the ninth communication system, then simultaneously transmit it alongside backchannel audio to all other dashboards connected to the same active session over the ninth communication system; the dashboard's fourth processor is also configured to receive GPS location originating from all the other dashboards connected to the same active session and its geolocation map is also configured to display the GPS location of all the other session dashboards as independent icons, each identifying its originating dashboard user.

The telemedicine system, wherein the gateway's third processor is also configured to transmit GPS location received from a dashboard alongside backchannel audio to an aggregator over the eighth communication system; the aggregator's second processor is also configured to receive GPS location from a gateway over its fifth communication system and its second display is also configured to display the GPS location of all session as independent icons, each identifying its originating dashboard user.

The telemedicine system, wherein the gateway's third application executed on the third processor is further configured to capture and store within the first persistent memory device a timestamped copy of all the GPS location data passing through the gateway.

A telemedicine method for allowing a plurality of medical teams assisting a plurality of patients to interact with and get assistance from a plurality of remote physicians via a plurality of audio, video, and streaming vital signs transmissions, comprising: monitoring one or more patients with patient monitoring devices, the patient monitoring device having one or more vital signs sensors configured for physical attachment to a patient; receiving vital signs information from the vital signs sensors, generating streaming vital signs based on the information from the vital signs sensors, and transmitting at least a first portion of the streaming vital signs to an aggregator while simultaneously displaying a representation of at least a second portion of the streaming vital signs on a first screen; receiving the streaming vital signs by one or more aggregators, the aggregator having one or more audio and video sensors and one or more first audio reproduction devices; transmitting at least a third portion of the streaming vital signs to a first gateway, capturing site audio and video from the aggregator's sensors while transmitting the site audio and video to a second gateway, and simultaneously receiving backchannel audio from a third gateway, displaying an aggregated representation of at least a fourth portion of the streaming vital signs together with the site video and session controls on a second screen, and reproducing the site audio combined with the backchannel audio through the first audio reproduction devices; receiving the site audio and video by a first gateway, maintaining session status, statistics, and configuration on the first gateway via a third screen, receiving streaming vital signs by a second gateway, and sending combined backchannel audio to the aggregator from a third gateway, maintaining session information relating to a source aggregator and one or more dashboards within the gateway, sending site audio and video combined with the streaming vital signs to one or more session dashboards while simultaneously receiving backchannel audio from one or more session dashboards and transmitting the combined backchannel audio to the source aggregator; receiving site audio and video and streaming vital signs by a dashboard, the dashboard having one or more audio sensors and one or more second audio reproduction devices, displaying an aggregated representation of at least a fifth portion of the streaming vital signs with a representation of the site video and session controls on a fourth screen, capturing audio backchannel from the dashboard's audio sensor and sending it back to the gateway, while simultaneously reproducing the site audio combined with the backchannel audio received as audible sounds on the dashboard's second audio reproduction devices.

The telemedicine method, wherein the first and second gateways are the same.

The telemedicine method, wherein the second and third gateways are the same.

The telemedicine method, wherein the first and second portions of the streaming vital signs data are the same.

The telemedicine method, wherein the second and third portions of the streaming vital signs data are the same.

The telemedicine method, wherein the third and fourth portions of the streaming vital signs data are the same.

The telemedicine method, wherein the fourth and fifth portions of the streaming vital signs data are the same.

The telemedicine method, wherein either of the patient monitoring devices are portable.

The telemedicine method, wherein either of the aggregators are portable.

The telemedicine method, wherein either of the gateways are portable.

The telemedicine method, wherein either of the dashboards are portable.

The telemedicine method, wherein either of the screens are touch-enabled.

The telemedicine method, wherein either of the gateways are cloud-based virtual server instances.

The telemedicine method, wherein either of the gateways are physical server instances, either on-site, collocated or cloud-based.

The telemedicine method, wherein either of the gateways are server cluster systems, and whereby the server cluster system is redirecting, recording, or modifying communication between transmitters and receivers with manual or automatic computing resource scaling.

The telemedicine method, wherein at least a portion of the data is transmitted using either Transmission Control Protocol/Internet Protocol (TCP/IP), User gram Protocol (UDP), Internet Control Message Protocol (ICMP), or their FastPath Stack successor in any combination thereof as baseline protocols.

The telemedicine method, wherein at least a portion of the data transmission is encrypted with a method including but not limited to the Secure Sockets Layer (SSL) protocol, Transport Layer Security (TLS), etc.

The telemedicine method, wherein at least a portion of the audio and/or video—is transmitted using the World Wide Web Consortium's (W3C) Web Real-Time Communication (WebRTC) protocol.

The telemedicine method, wherein at least a portion of the streaming vital signs data is transmitted using the Internet Engineering Task Force's (IETF) WebSocket protocol.

The telemedicine method, wherein access to either of the communication systems is protected with either single or multiple factor authentication schemes consisting of a user ID/password, a digital certificate such as the Public Key Infrastructure (PKI)-based X.509 certificate, a biometric reading such as the image of a fingerprint, a retinal scan, facial recognition, or any combination thereof.

The telemedicine method, wherein the audio, video, and streaming vital signs is partitioned for transmission in fixed size packets each representing a time interval configurable to any value between 20 milliseconds and 2 seconds.

The telemedicine method, wherein new packets of either audio, video, or vital signs data are transmitted at constant time intervals, programmable between 40 to 960 milliseconds.

The telemedicine method, wherein either of the data packets transmitted over either of the communication systems is structured according to JavaScript Object Notation (JSON) specification.

The telemedicine method, wherein either of the packets transmitted is compressed using a lossless compression algorithm like Huffman Coding, arithmetic coding, context-free weighing (CTW), RunLength Limited (RLL), Lempel-Ziv 77 (LZ77), Lempel-Ziv 78 (LZW78), Lempel-Ziv-Storer-Symanski (LZ SS), Lempel-Ziv-Markov (LZM), Lempel-Ziv-Welch (LZW), Burrows-Wheeler Transform (BZT), Brotti, Zopfli, Sequitur, Prediction by Partial Matching (PPM) etc. or any component, combination, or derivative thereof, such as zip, gzip, pkzip, arc, rar, etc.

The telemedicine method, wherein waveforms such as 3, 5, 7, or 12-lead electrocardiogram (ECG), respiration, invasive blood pressure, and temperature; trending numeric parameters such as blood oxygen saturation level (SPO2), End-Tidal CO2 (EtCO2), heart rate, respiration rate, non-invasive blood pressure, temperature, streaming ultrasound images, streaming endoscopic images, stethoscope ascultation patterns, etc.; patient monitor generated alarms such as ventricular fibrillation, etc. and patient monitor generated alerts such as blood pressure lower than a preset alert limit, etc.

The telemedicine method, wherein either of the patient monitoring devices is a monitor-defibrillator.

The telemedicine method, wherein a timestamped copy of all the site audio, video, backchannel audio, and streaming vital signs data passing through the gateway is stored within a first persistent memory device on the gateway.

The telemedicine method, wherein the dashboard also reads user input and transmits pause, play back, rewind, and fast forward commands to the gateway, and the gateway also reads the timestamped site audio, video, backchannel audio, and streaming vital signs stored in its first persistent memory device, applies a controlled time offset for each such function requested, sends it back to the requesting dashboard, and the dashboard also displays the received video on its fourth screen and renders the received audio through its second audio reproduction device.

The telemedicine method, wherein the gateway also stores within the first persistent memory device a timestamped copy of all the site audio, video, backchannel audio, textual chat messages, and streaming vital signs data received by the gateway even if it loses connectivity with the dashboard, and makes it available to the dashboard under its request and control when the dashboard reconnects with the gateway.

The telemedicine method, wherein the aggregator also stores a timestamped copy of all the site audio, video, and streaming vital signs received by the aggregator in a second persistent memory device even when it loses connectivity with the gateway, and when it reconnects with the gateway, also sends the stored (catch-up) to the gateway in parallel with its normal transmission, in a catch-up mode, until all the catch-up is exhausted, and the gateway also inserts and stores the received catch-up, in its correct timestamp order, on its first persistent memory device.

The telemedicine method, wherein the gateway also groups a plurality of gateway login accounts and a plurality of dashboard login accounts into Virtual Medical Groups (VMG), only allowing the communication of site audio, video, backchannel audio, and vital signs between the gateways and dashboards where the users logged in belong to the same VMG, and wherein the gateway allows a system administrator to create, modify, and remove VMGs through the allocation and deallocation of individual gateway and dashboard login accounts to VMGs, in either an exclusive or a shared fashion.

The telemedicine method, wherein the aggregator also reads its location position from a first GPS sensor, initiates an assistance request combined with its GPS position indicating the type of expertise sought, and transmits such assistance request to one or more gateways; the gateway also receives such assistance requests and forwards them to one or more of the dashboards whose logged in users belong to the same VMG as the user logged into the requesting gateway and according to a preprogrammed priority based on their type of expertise registered with the system; the dashboard also displays the assistance request on a geolocation map using the GPS information embedded in the assistance request, waits for the logged in user to confirm, and if confirmed within a programmed window of time, initiates an end-to-end audio, video, and streaming vital signs session between the dashboard and the requesting aggregator through the connecting gateway. If the user does not confirm the assistance request within the preprogrammed time, the gateway forwards the assistance request, according to a preprogrammed escalation logic and based on their type of expertise registered with the system, to another dashboard whose logged in user belongs to the same VMG as the requesting gateway's logged in user. If no dashboard with a logged in user belonging to the same VMG as the requesting gateway's logged in user exists at that time, the gateway hails the next recipient, according to a programmed escalation logic and based on their type of expertise registered with the system, through an external channel including but not limited to, a SMS message over a cellular network, an e-mail, a text-to-speech voice message over a cellular or traditional phone network, etc. The dashboard also displays the pending assistance request on a geolocation map using the GPS information embedded in the assistance request when the user hailed though an external channel logs into the dashboard, waits for the logged in user to confirm, and if confirmed within a programmed window of time, initiates an end-to-end audio, video, and streaming vital signs session between the dashboard and the requesting aggregator through the connecting gateway.

The telemedicine method, wherein a dashboard user providing assistance to an aggregator user through an active end-to-end session sends a secondary assistance request based on the same or different requested second skill set to another nominated or generic user from the same VNG, and the gateway receives such a secondary assistance request and dispatches it to the nominated user or to the next qualified user from the same VMG and according to its programmed escalation logic. The dashboard also displays the secondary user's pending assistance request on a geolocation map using the GPS information embedded in the original assistance request, waits for the secondary user to confirm, and if confirmed within a programmed window of time, initiates a secondary dashboard session with the same gateway user as the dashboard user placing the secondary assistance request. When the dashboard is in such a secondary assistance mode, it displays a replica of the primary session's streaming waveforms, trending parameters, clinical alarms and alerts, and site video, and reproduces a replica of the site audio combined with the composite backchannel audio originating from all session dashboards.

The telemedicine method, wherein the gateway also combines all backchannel audio originating from the primary and all secondary dashboard users providing assistance to the same gateway user, and sends the combined audio backchannel forward to the aggregator and back to the primary and all secondary dashboards connected to the same gateway session.

The telemedicine method, wherein the site audio, video, and streaming vital signs data are partitioned in packets each representing such data originating within the same 40 to 960 milliseconds time interval, and whereby all such packets are further combined in a single composite data packet that encompasses all site audio, video, and streaming vital signs originating within the said time interval.

The telemedicine method, wherein the composite data packet (payload) is further compressed to reduce its size, and whereby the compressed packet may also include derived information used to detect the tampering and/or corruption of the payload including, but not limited to, an electronic signature performed with the aid of symmetric or asymmetric key scheme, a hash, a checksum, a digital watermark, a cryptographic timestamp, etc.

The telemedicine method, wherein the dashboard also sends a 12 Lead analysis request to the gateway, the gateway also takes a snapshot of ECG from its first persistent memory device, performs a 12-Lead analysis through a third party analysis module including, but not limited to, GE-Marquette 12SL, Glasgow 12-Lead ECG Analysis, Zoll Inovise, Philips EASI, etc., generates a 12 Lead ECG analysis report, and sends such report back to the dashboard, and the dashboard also receives the 12 Lead analysis report, and renders it on its fourth display.

The telemedicine method, wherein the gateway also archives the generated 12 Lead ECG analysis report into the gateway's first persistent memory device, the dashboard also sends a retrieval command for a previously generated 12 Lead ECG analysis to the gateway, the gateway also responds to a retrieval command of a previously generated 12 Lead ECG analysis report and sends such report to the dashboard, and the dashboard receives the said 12 Lead analysis report from the gateway and renders it on its fourth display.

The telemedicine method, wherein the 12 Lead ECG analysis is substituted with any derivative calculation, analysis, alarm, or alert executed across any number of streaming vital signs, including but not limited to, ECG, temperature, invasive blood pressure, and respiration waveforms, trending numerical parameters such as EtCO2, SPO2, temperature, streaming ultrasound or endoscopic images, auscultation waveforms, respiration rate, heart rate, non-invasive blood pressure, etc. and/or including patient monitor generated alarms and alerts.

The telemedicine method, wherein the gateway uses machine learning algorithms included but not limited to, neural networks, fuzzy logic, artificial intelligence, etc. based on previously stored streaming vital signs received from at least a portion of all the other patients' vital signs received and stored in its first persistent memory device to improve the accuracy of at least a portion of all of its derivative calculations, analyses, alarms, or alerts.

The telemedicine method, wherein the gateway uses for its machine learning algorithms externally provided historical streaming vital signs data either preloaded into the gateway's first persistent memory device or downloaded from an data provider, or a combination of internally stored and externally accessed such.

The telemedicine method, wherein the dashboard also captures a new time stamped textual or voice recorded annotation event and sends it to the gateway, the gateway also receives the time stamped textual and/or voice recording annotation event and stores it into the gateway's first persistent memory device alongside the currently recorded site audio, video, and streaming vital signs-, the dashboard also captures a textual or voice search request for a previously stored annotation event and sends it to the gateway, the gateway also responds to a voice or textual retrieval command of a previously stored annotation event by generating a search specification based on an algorithm including, but not limited to, voice recognition, text to speech, neural networks, fuzzy logic, artificial intelligence, Boolean, binary tree, etc., searching based on the generated search specification and its associated algorithm, locating, and sending such previously stored annotation event together with all the previously stored backchannel audio, site audio, video, and streaming vital signs in a configurable time window surrounding the time stamp of the first annotation event match back to the dashboard, and the dashboard also receives the said previously stored annotation event together with all the previously stored site audio, video, and streaming vital signs from its configurable time window from the gateway and renders it on its fourth display.

The telemedicine method, wherein the dashboard also captures a search request to be executed over the site and/or backchannel voice recorded in the gateway's first persistent storage device and sends it to the gateway, the gateway also applies its generated search criteria to the site and/or backchannel voice recorded in the gateway's first persistent storage device and sends such previously stored backchannel audio, site audio, video, and streaming vital signs in a configurable time window surrounding the time stamp of the first match back to the dashboard, and the dashboard receives the said backchannel audio, site audio, video, and streaming vital signs from its configurable time window from the gateway and renders it on its fourth display.

The telemedicine method, wherein the dashboard also requests the first, last, next, or previous such search's match, and the gateway also sends either the first, last, next, or previous such search's match, as requested, back to the dashboard.

The telemedicine method, wherein the aggregator also captures a textual or voice search request for a procedural guidance and sends it to the gateway, the gateway also responds to such a request by generating a search specification based on an algorithm including, but not limited to, voice recognition, text to speech, neural networks, fuzzy logic, artificial intelligence, Boolean, binary tree, etc., searching based on the generated search specification and its associated algorithm, locating and retrieving a previously stored procedural guidance including, but not limited to, text, hypertext, annotated text, structured text, images, audio, video, or any combination thereof, and sending the first match of such previously stored procedural guidance to the requesting aggregator, and the aggregator also renders the received procedural guidance in its appropriate representation, whether text, images, audio, video, or any combination thereof, either as standalone or as an overlay.

The telemedicine method, wherein the gateway also searches and retrieves procedural guidance data downloaded from an external data provider, or a combination of internally stored and externally accessed procedural guidance data.

The telemedicine method, wherein the aggregator also requests the first, last, next, or previous such search's match, and the gateway also locates and sends to the aggregator either the first, last, next, or previous such search's match, as requested.

The telemedicine method, wherein the gateway also displays the said procedural guidance data received from the gateway on a portable augmented reality display including, but not limited to, headset, goggle, retinal scanning device, smart glass eyewear such as Google Glass, Microsoft HoloLens, Sony SmartGlass, etc.

The telemedicine method, wherein the gateway also triggers and actuates a built-in haptic feedback device in response to a selection of preprogrammed biological conditions detected in the streaming vital signs being displayed including, but not limited to, heart beats, respiratory cycles, preprogrammed biological parameter limits such as temperature, EtCO2, SPO2, invasive blood pressure being reached, etc., and when patient monitor-generated alarm or alert conditions are being detected as part of the streaming vital signs being displayed.

The telemedicine method, wherein the dashboard also triggers and actuates a built-in haptic feedback device in in response to a selection of preprogrammed biological conditions detected in the streaming vital signs being displayed including, but not limited to, heart beats, respiratory cycles, preprogrammed biological parameter limits such as temperature, EtCO2, SPO2, invasive blood pressure being reached, etc., and when patient monitor-generated alarm or alert conditions are being detected as part of the streaming vital signs being displayed.

The telemedicine method, wherein the haptic feedback pattern is programmed to be unique for each group or individual type of biological conditions, alarms, or alert triggers.

The telemedicine method, wherein the dashboard also captures streaming video from a built-in video sensor and transmits it as backchannel video alongside backchannel audio to a gateway; the gateway also receives backchannel video alongside backchannel audio from a dashboard, then transmits the received backchannel video alongside backchannel audio to an aggregator and simultaneously to all other dashboards connected to the same active session; the dashboard also receives backchannel video originating from all the other dashboards connected to the same active session and renders the backchannel video originating from all the other session dashboards in independent sections on its fourth display, each identifying its originating dashboard user; the aggregator also receives backchannel video from a gateway and renders the backchannel video originating from all session dashboards in independent sections on its second display, each identifying its originating dashboard user.

The telemedicine method, wherein the gateway also captures and stores within the first persistent memory device a timestamped copy of all the backchannel video data passing through it.

The telemedicine method, wherein the dashboard also captures GPS location from a built-in GPS sensor and transmits it as GPS alongside backchannel audio to a gateway; the gateway also receives GPS location alongside backchannel audio from a dashboard, then simultaneously transmits it alongside backchannel audio to all other dashboards connected to the same active session; the dashboard also receives GPS location originating from all the other dashboards connected to the same active session and displays on its geolocation map the GPS location of all the other session dashboards as independent icons, each identifying its originating dashboard user.

The telemedicine method, wherein the gateway also transmits GPS location data received from a dashboard alongside backchannel audio to an aggregator; the aggregator also receives GPS location data from a gateway and displays the GPS location of all session as independent icons, each identifying its originating dashboard user, on its second display.

The telemedicine method, wherein the gateway also captures and stores within its first persistent memory device a timestamped copy of all the GPS location data passing through the gateway.

The telemedicine method, wherein the gateway also exports any and all of its stored audio, video, vital signs, and GPS data to an external memory device and also makes it available for retrieval through a Web page, a Web service, or a TCP socket interface.

The telemedicine method, wherein the patient monitor and the aggregator are the same.

While multiple embodiments are discussed, still other embodiments of the present invention will become apparent to those skilled in the art from the following detailed description, which shows and describes illustrative embodiments of the invention, Accordingly, the drawings and detailed description are to be regarded as illustrative in nature and not restrictive.

While the invention is amenable to various modifications and alternative forms, specific embodiments have been shown as examples by the way of the drawings and are described in detail below. The invention is, however, intended to cover all modifications, equivalents, and alternatives falling within the scope of the invention as defined by the appended claims, and thus not limited to neither the particular embodiments nor the particular examples discussed herein.

DETAILED DESCRIPTION

Figure 1:
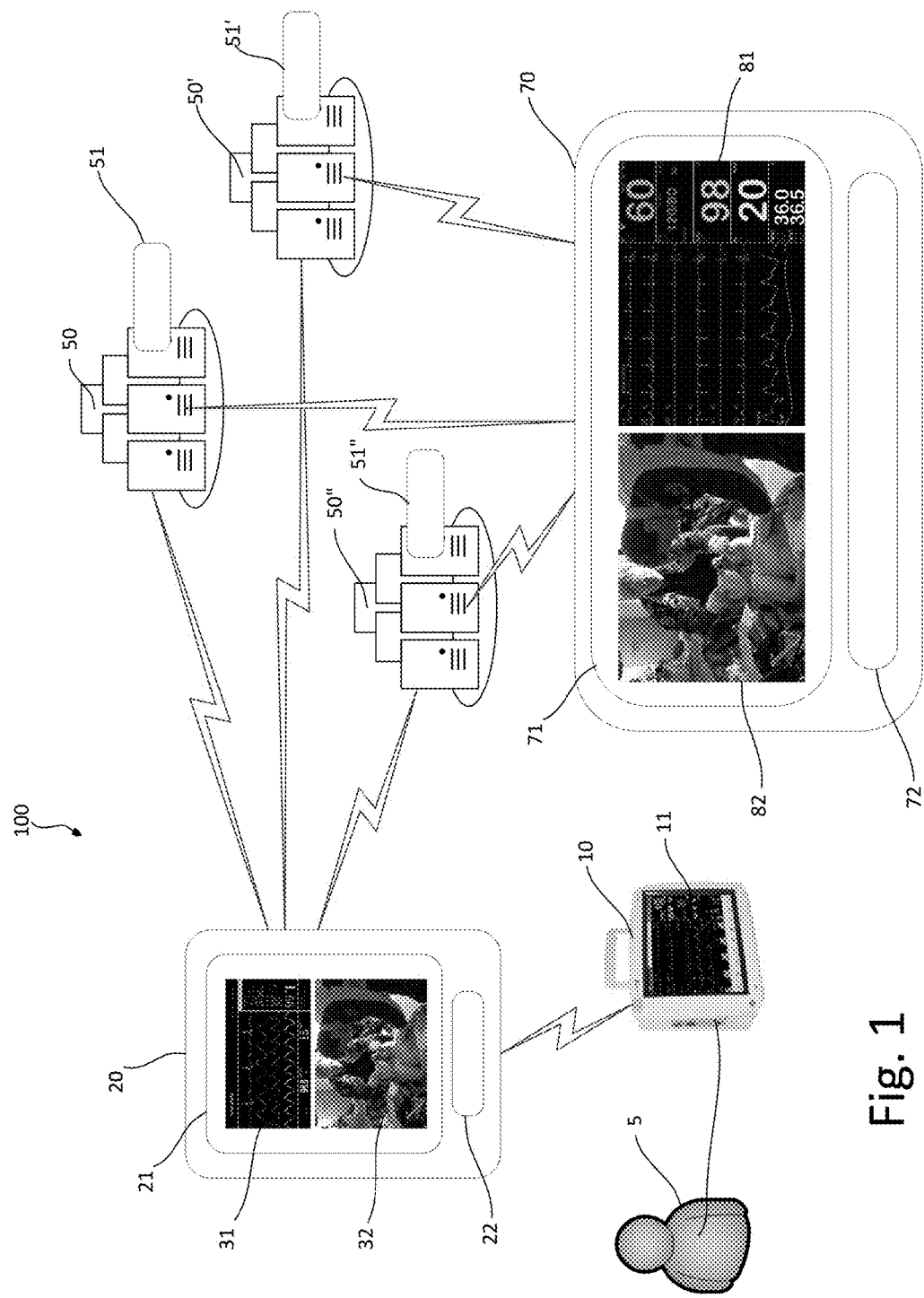
FIG. 1 illustrates a vital-signs enhanced distributed telemedicine system, whereby, according to some embodiments of the present invention, the streaming vital signs and the site audio and video are transmitted from the aggregators to separate gateways over two separate communication systems, and backchannel audio, video, and GPS data are received by the aggregators from separate gateways over a third communication system.

FIG. 1 illustrates a vital-signs enhanced distributed telemedicine system 100, including a patient monitoring device 10, configured for physical attachment to patient 5, communicating with an aggregator 20, which is communicating with a first gateway 50, a second gateway 50', and a third gateway 50", which are further communicating to a dashboard 70, according to embodiments of the present invention. The monitoring device 10 may include a display screen 11 configured to display vital signs information about the patient 5, according to embodiments of the present invention. The aggregator 20 may include a display screen 21 configured to display vital signs information received in its monitoring pane 31, video from its video sensing device in its video pane 32, and render backchannel audio received from a gateway through its audio reproducing device 22, according to embodiments of the present invention. The gateways 50, 50', and 50" may include a display screen 51, 51', and 51" respectively, configured to display status and configuration information, according to embodiments of the present invention. The dashboard 70 may include a display screen 71 configured to display vital signs information received in its monitoring pane 81, video received in its video pane 82, and render audio received from a gateway through its audio reproducing device 72, according to embodiments of the present invention.

Figure 2:
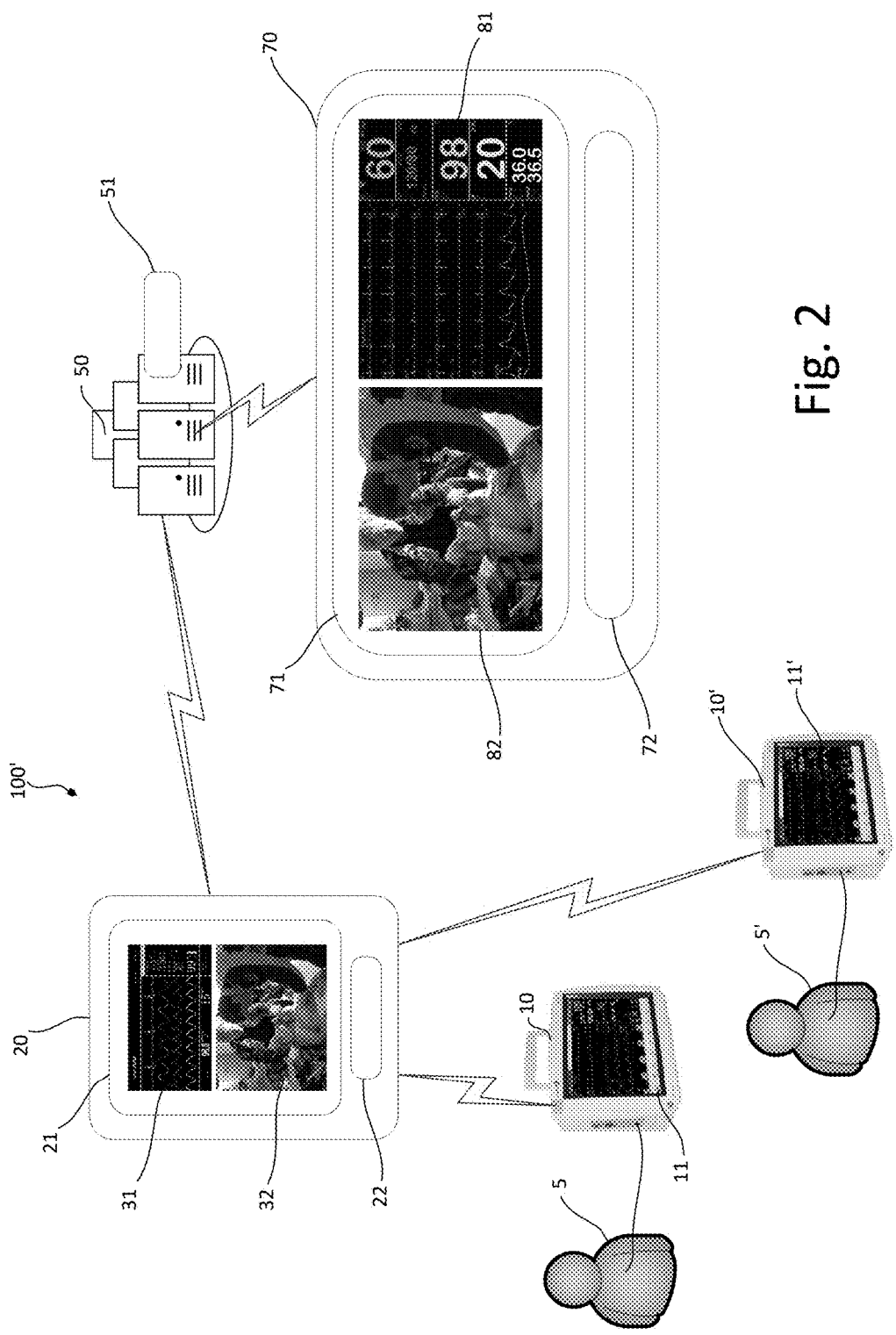
FIG. 2 illustrates a vital-signs enhanced distributed telemedicine system, whereby, according to some embodiments of the present invention, the streaming vital signs and the site audio and video are transmitted from the aggregators to the same gateways over the same communication system, and backchannel audio, video, and GPS data are received by the aggregators from the same gateways over the same communication system as well.

FIG. 2 illustrates a vital-signs enhanced telemedicine system 100', including two patient monitoring devices 10 and 10', configured for physical attachment to patients 5 and 5', respectively, communicating with an aggregator 20, which is communicating with a gateway 50, which is further communicating to a dashboard 70, according to embodiments of the present invention. The monitoring devices 10 and 10' may include a display screen 11 and 11', respectively, configured to display vital signs information about the patients 5 and 5', respectively, according to embodiments of the present invention. The aggregator 20 may include a display screen 21 configured to display vital signs information received in its monitoring pane 31, video from its video sensing device in its video pane 32, and render backchannel audio received from a gateway through its audio reproducing device 22, according to embodiments of the present invention. The gateway 50 may include a display screen 51 configured to display status and configuration information, according to embodiments of the present invention. The dashboard 70 may include a display screen 71 configured to display vital signs information received in its monitoring pane 81, video received in its video pane 82, and render audio received from a gateway through its audio reproducing device 72, according to embodiments of the present invention.

Figure 3:
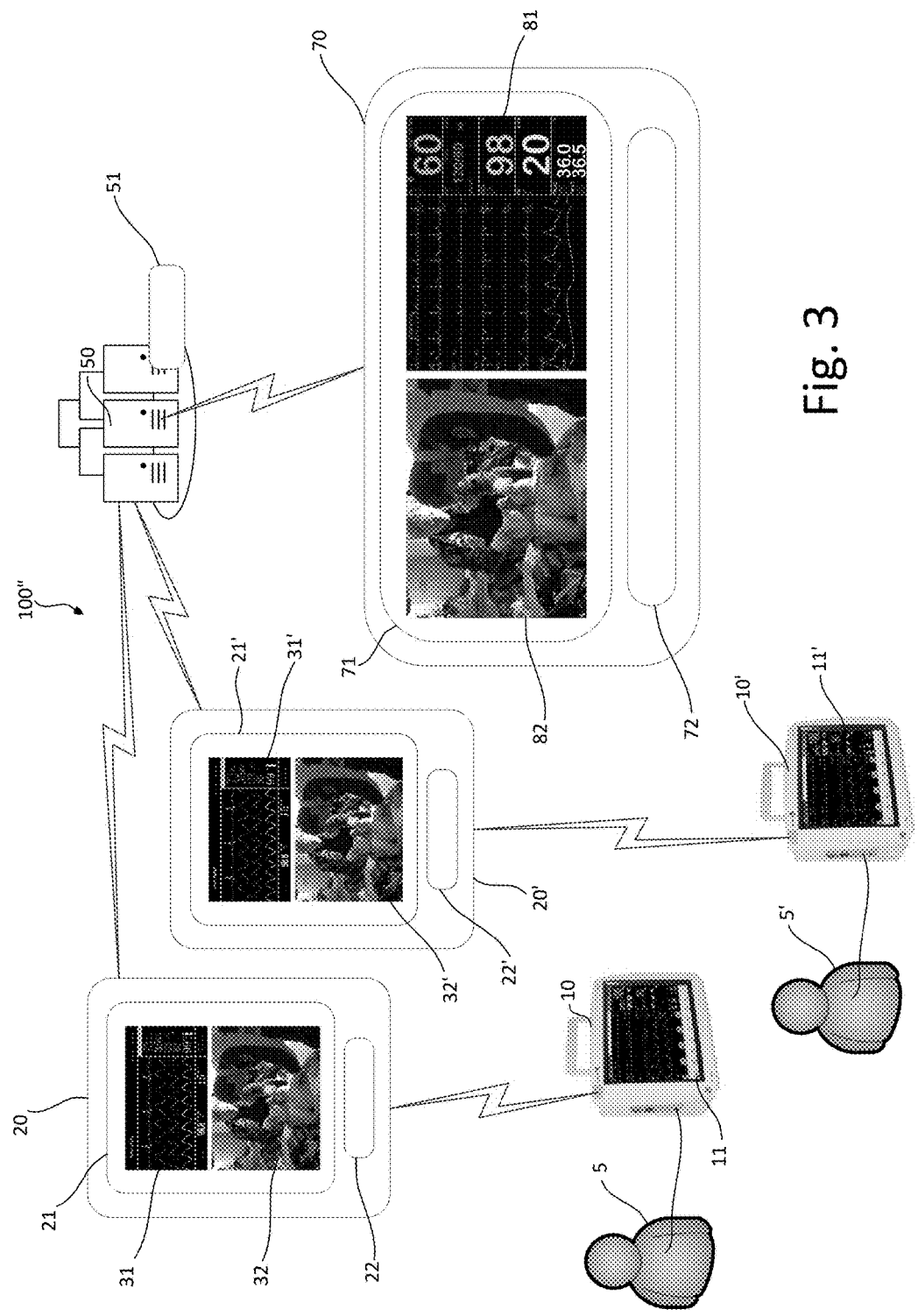
FIG. 3 illustrates a vital-signs enhanced distributed telemedicine system, whereby, according to some embodiments of the present invention, the streaming vital signs and the site audio and video are transmitted from the aggregators to the gateways over the same communication system, the backchannel audio, video, and GPS are received by the aggregators from the gateways over the same communication system, and one dashboard connects, alternatively, with two concurrent remote assistance sessions originating from two separate gateways.

FIG. 3 illustrates a vital-signs enhanced distributed telemedicine system 100", including two patient monitoring devices 10 and 10', configured for physical attachment to patients 5 and 5', respectively, communicating with two aggregators 20 and 20', respectively, which are communicating with a gateway 50, which is further communicating to a dashboard 70, according to embodiments of the present invention. The monitoring devices 10 and 10' may include a display screen 11 and 11', respectively, configured to display vital signs information about the patients 5 and 5', respectively, according to embodiments of the present invention. The aggregators 20 and 20' may include a display screen 21 and 21', respectively, configured to display vital signs information received in its monitoring pane 31 and 31', respectively, video from its video sensing device in its video pane 32 and 32', respectively, and render backchannel audio received from a gateway through its audio reproducing device 22 and 22', respectively, according to embodiments of the present invention. The gateway 50 may include a display screen 51 configured to display status and configuration information, according to embodiments of the present invention. The dashboard 70 may include a display screen 71 configured to display vital signs information received in its monitoring pane 81, video received in its video pane 82, and render audio received from a gateway through its audio reproducing device 72, according to embodiments of the present invention.

Figure 4:
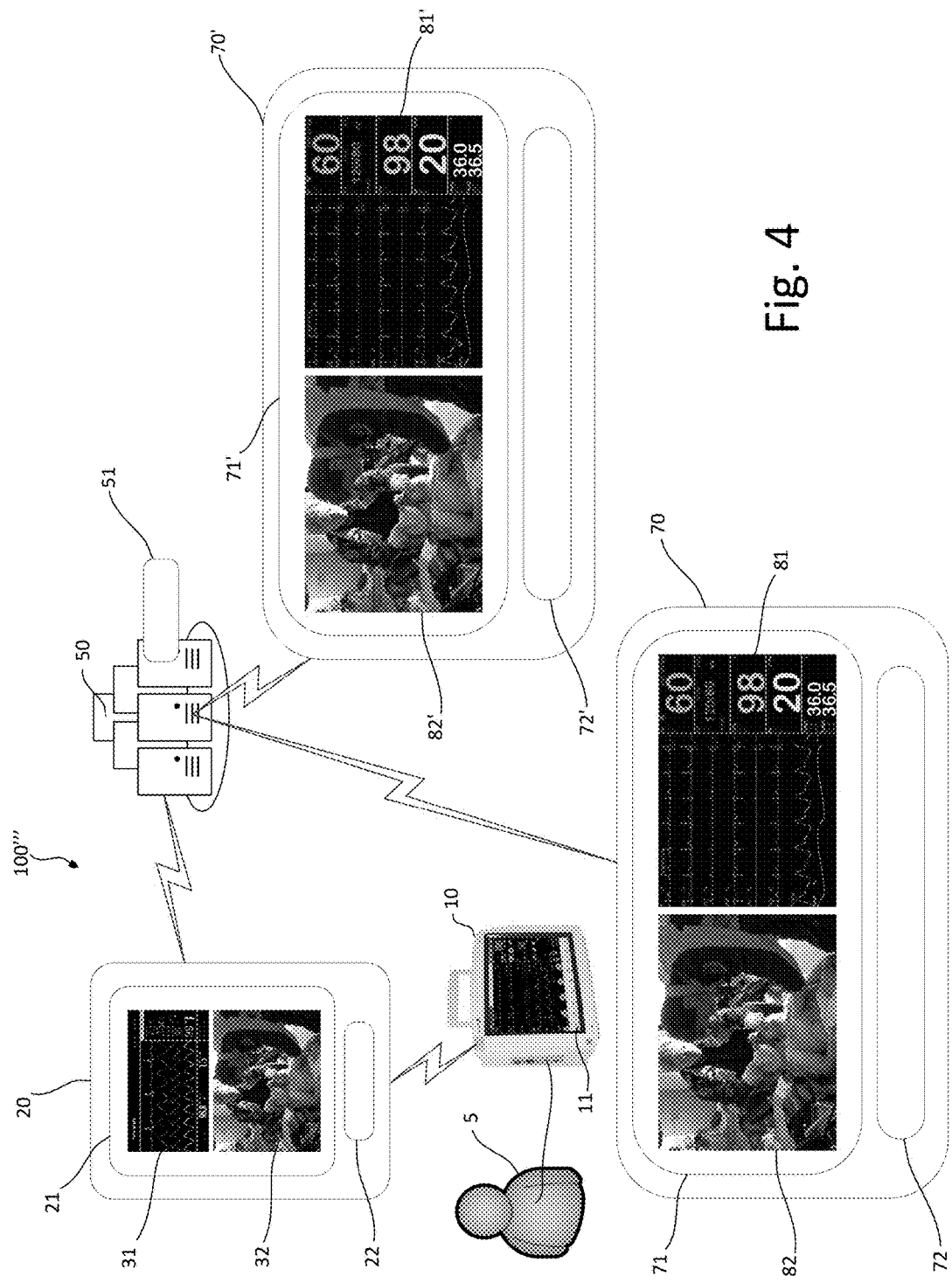
FIG. 4 illustrates a vital-signs enhanced distributed telemedicine system, whereby, according to some embodiments of the present invention, the streaming vital signs and the site audio and video are transmitted from the aggregators to the gateways over the same communication system, the backchannel audio, video, and GPS are received by the aggregators from the gateways over the same communication system as well, and two dashboards participate concurrently in the same remote assistance session originating from the same gateway.

FIG. 4 illustrates a vital-signs enhanced telemedicine system 100''', including a patient monitoring device 10, configured for physical attachment to patient 5, communicating with an aggregator 20, which is communicating with a gateway 50, which is further communicating to dashboards 70 and 70', according to embodiments of the present invention. The monitoring device 10 may include a display screen 11 configured to display vital signs information about the patient 5, according to embodiments of the present invention. The aggregator 20 may include a display screen 21 configured to display vital signs information received in its monitoring pane 31, video from its video sensing device in its video pane 32, and render backchannel audio received from a gateway through its audio reproducing device 22, according to embodiments of the present invention. The gateway 50 may include a display screen 51 configured to display status and configuration information, according to embodiments of the present invention. The dashboards 70 and 70' may include a display screen 71 and 71', respectively, configured to display vital signs information received in its monitoring pane 81 and 81', respectively, video received in its video pane 82 and 82', respectively, and render audio received from a gateway through its audio reproducing device 72 and 72', respectively, according to embodiments of the present invention.

Figure 5:
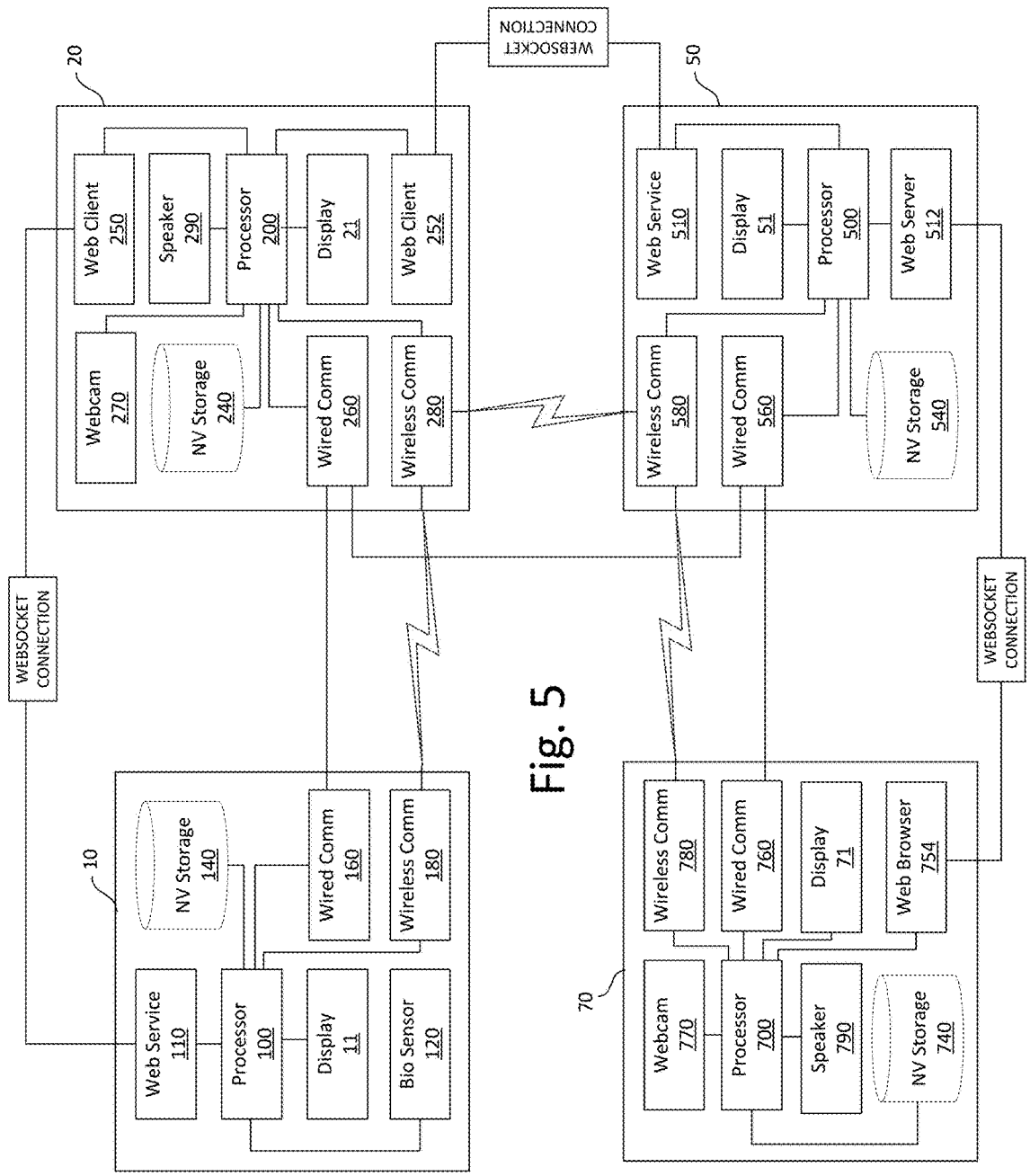
FIG. 5 illustrates a vital-signs enhanced distributed telemedicine system whereby the main internal blocks of a patient monitor, aggregator, gateway, dashboard, and their internal and external connections are identified.

FIG. 5 illustrates a patient monitoring device 10, an aggregator 20, a gateway 50, and a dashboard 70, according to embodiments of the present invention. Patient monitoring device 10 may include one or more bio sensors 120 configured for physical attachment to a patient, a processor 100 configured to receive information from one or more sensors 120 and to generate streaming vital signs based on the information, a web service 110, a wired communication system 160, a wireless communication system 180, a non-volatile storage device 140, and a display 11 configured to display at least a portion of the patient's vital signs, according to embodiments of the present invention. Aggregator 20 may include a processor 200 configured to receive audio-video information from a built-in webcam 270, a monitor-facing web client 250, a gateway-facing web client 252, a wired communication system 260, a wireless communication system 280, a non-volatile storage device 240 for storing catch-up, a display 21 configured to display at least a portion of the patient's vital signs and the video from the Webcam 270, and a speaker 290 configured to render backchannel audio received from the gateway 50, according to embodiments of the present invention. Gateway 50 may include a processor 500 configured to maintain session information across a plurality of aggregators 20 and dashboards 70, an aggregator-facing web service 510, a dashboard-facing web server 512, a wired communication system 560, a wireless communication system 580, a non-volatile storage device 540 for persistent storage of all sessions' audio, video, and vital signs, and a display 51 configured to display session status and configuration information, according to embodiments of the present invention. Dashboard 70 may include a processor 700 configured to receive audio-video information from a built-in webcam 770, a web browser 754, a wired communication system 760, a wireless communication system 780, a non-volatile storage device 740, a display 71 configured to display at least a portion of the patient's vital signs and the video received from the gateway 50, and a speaker 790 configured to render audio received from the gateway 50, according to embodiments of the present invention.

Figure 6:
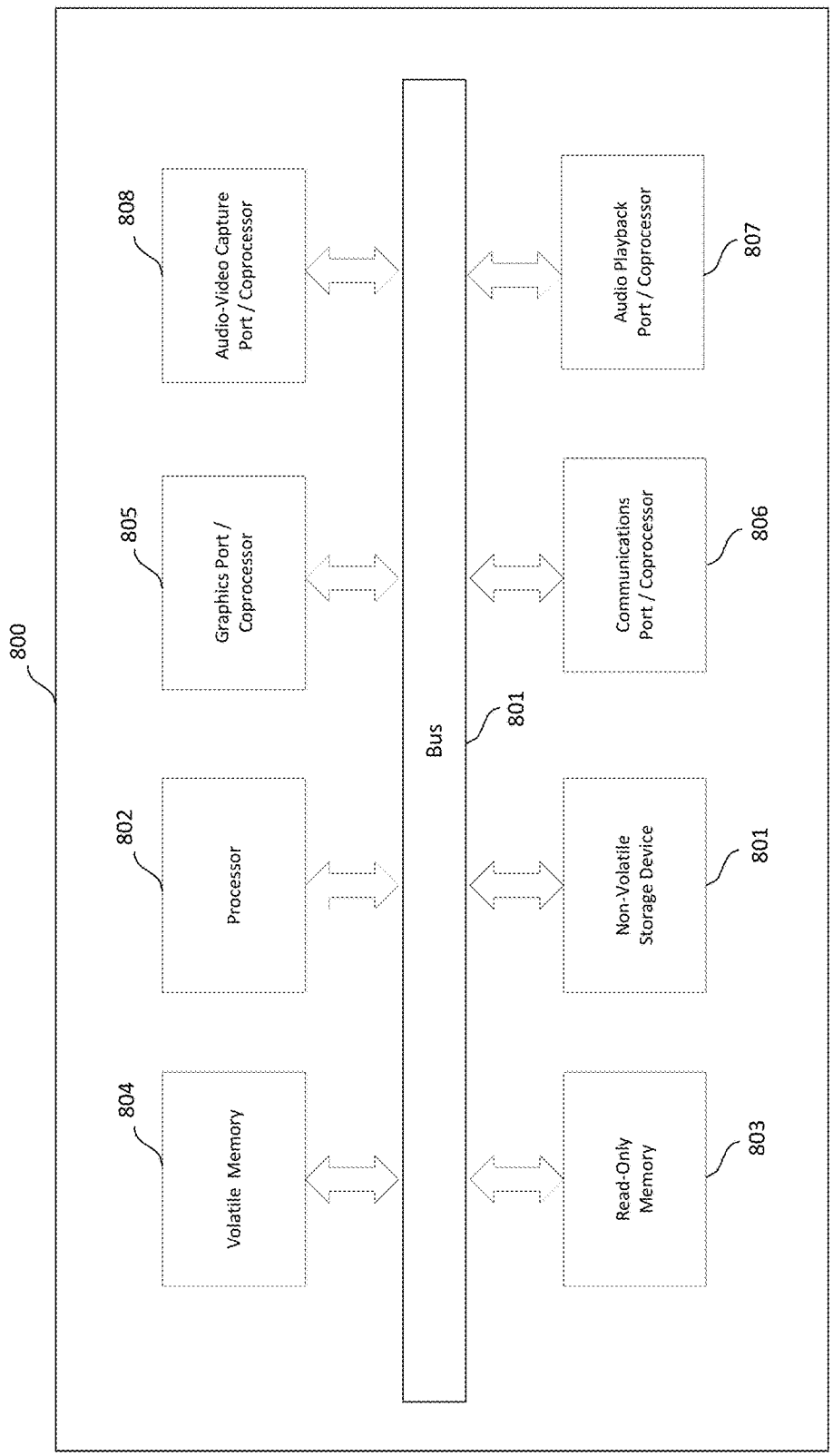
FIG. 6 illustrates a computer system that can constitute the platform for a patient monitor, aggregator, and/or dashboard, according to the embodiments of the present invention.

FIG. 6 is an example of a computer system 800 with which embodiments of the present invention may be utilized. For example, patient monitors 10, aggregators 20, gateways 50, and dashboards 70 may be or incorporate a computer system 800, according to embodiments of the present invention. According to the present example, the computer system includes a bus 801, at least one processor 802, at least one communication port or coprocessor 806, a main volatile memory 804 for code execution and transient storage, a read-only memory 803 for initial boot and/or program storage, at least one non-volatile storage device 801 for persistent storage of programs, session audio, video, streaming vital signs, and GPS, instructional, analysis input, etc., an audio-video capture port or coprocessor 808, and an audio playback port or coprocessor 807, according to embodiments of the present invention.

Figure 7:
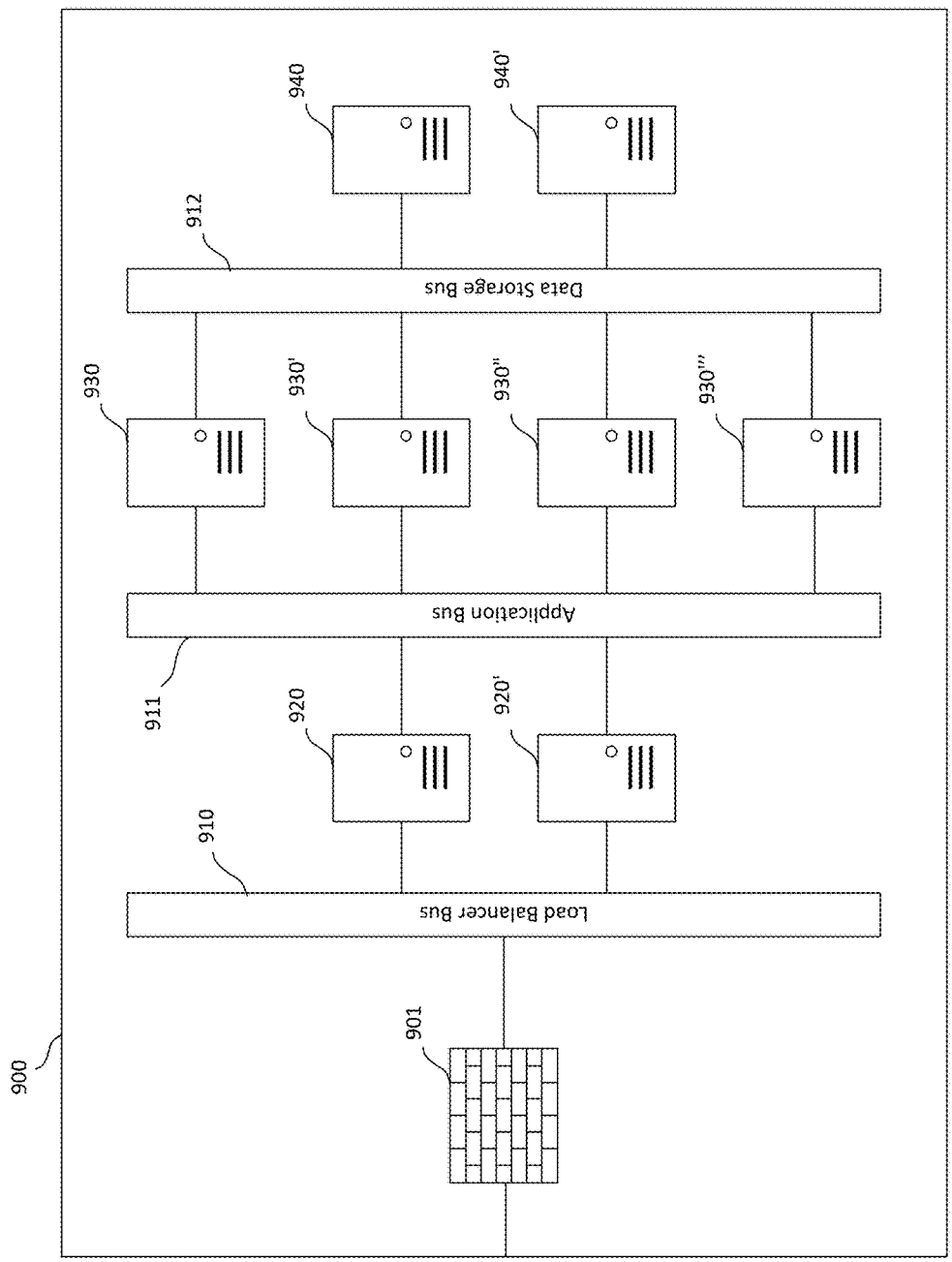
FIG. 7 illustrates a server cluster system that can constitute the platform for a gateway, according to the embodiments of the present invention.

FIG. 7 is an example of a server cluster system 900 that can constitute the platform for a gateway, according to some of the embodiments of the present invention. According to the present example, the server cluster 900 may contain an input firewall appliance 901, a load balancer bus 910, at least two front-end servers 920 and 920', an application bus 911, at least four application servers 930, 930', 930" and 930'", a storage bus 912, and at least two storage servers 940 and 940', whereby the firewall appliance 901 and each of the servers 920, 930, and 940 can have a configuration similar to the computer system 800 or an enhanced alternative thereof.

Figure 8:
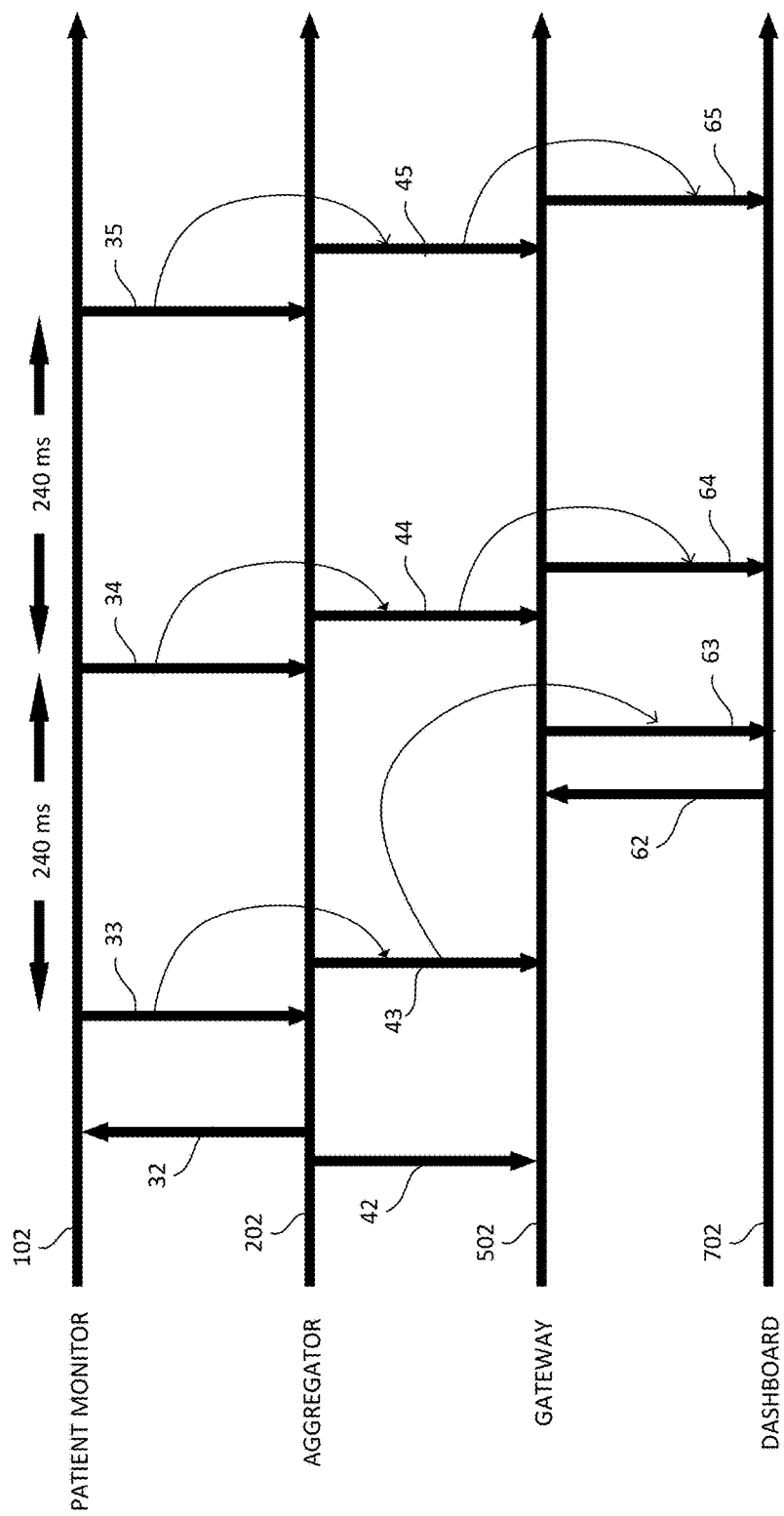
FIG. 8 illustrates communication and timing between a patient monitor, aggregator, gateway, and dashboard, according to the embodiments of the present invention.

FIG. 8 illustrates communication and timing between a patient monitor 102, aggregator 202, gateway 502, and dashboard 702, according to the embodiments of the present invention. For example, the aggregator may send a connection request 42 (which may also include a request for clinical assistance element) to the gateway 502 which establishes a session between the aggregator and the gateway, then send a connection request 32 to the patient monitor 102 which establishes a local session between the aggregator 202 and the patient monitor 102. The sequencing of the connection requests 42 and 32 can also be reversed, and someone skilled in the art would easily recognize. Once the local session between the patient monitor 102 and the aggregator 202 is established, the patient monitor 102 starts sending to the aggregator 202 packets 33, 34, 35, etc. consisting of vital signs information, alarms, and alerts, at regular time intervals, for example 240 milliseconds in duration, according to embodiments of the present invention. The interval between these packets can be programmed to any value from 40 to 960 milliseconds, according to embodiments of the present invention. Upon receipt of packets 33, 34, and 35 from the patient monitoring device 102, the aggregator 202 passes then on further to the gateway 502 as packets 43, 44, and 45, respectively. If a session between the gateway 502 and the dashboard 702 is not in place yet, like for example in the case of packet 43, the gateway 502 will store these packets internally. When the dashboard 702 sends a connection request 62 to the gateway 502 which connects the dashboard 702 to a previously established session between the same gateway 502 and the requesting aggregator 202, the aggregator 202 starts relaying any pending packets received from the patient monitor 102 to the gateway 502, but only if the pending packets are not overwritten by newer such packets received from the patient monitor 102, in order to avoid the transmission of "stale" audio, video, and vital signs. Upon receipt of such packets 43, 44, and 45 from the aggregator 202, the gateway 502 relays them further to the dashboard 702 as packets 63, 64, and 65, respectively. To keep the timing diagram simple, and also because this would be very easy for someone skilled in the art to envision, the catch-up transmission of "stale" data packets interleaved with the transmission of "live" data packets from the aggregator 202 to the gateway 502 is not depicted here.

Figure 9:
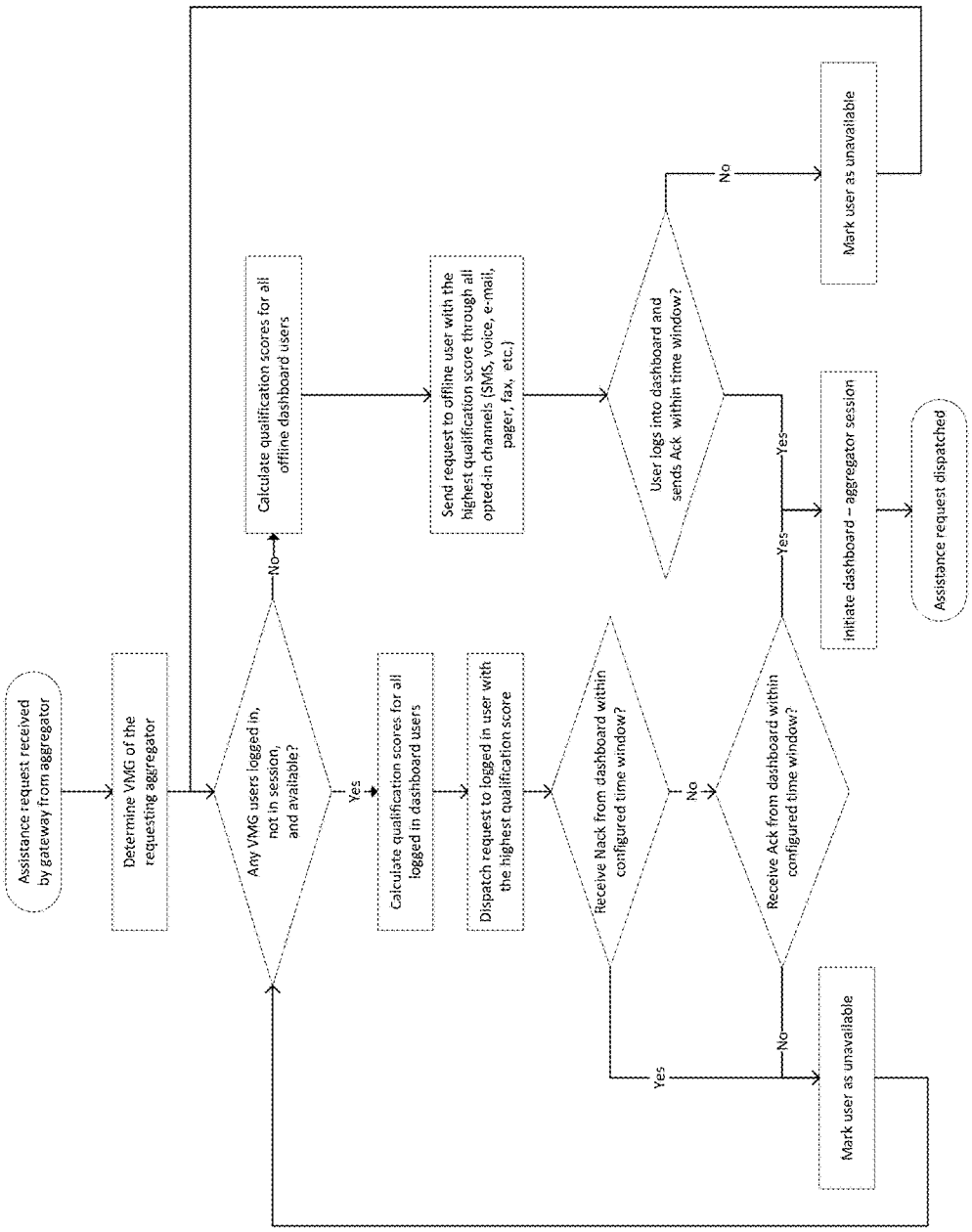
FIG. 9 illustrates a typical assistance request and escalation logic and workflow for a gateway, according to the embodiments of the present invention.

FIG. 9 illustrates a typical assistance request and escalation logic and workflow for a gateway, according to the embodiments of the present invention.

Figure 10:
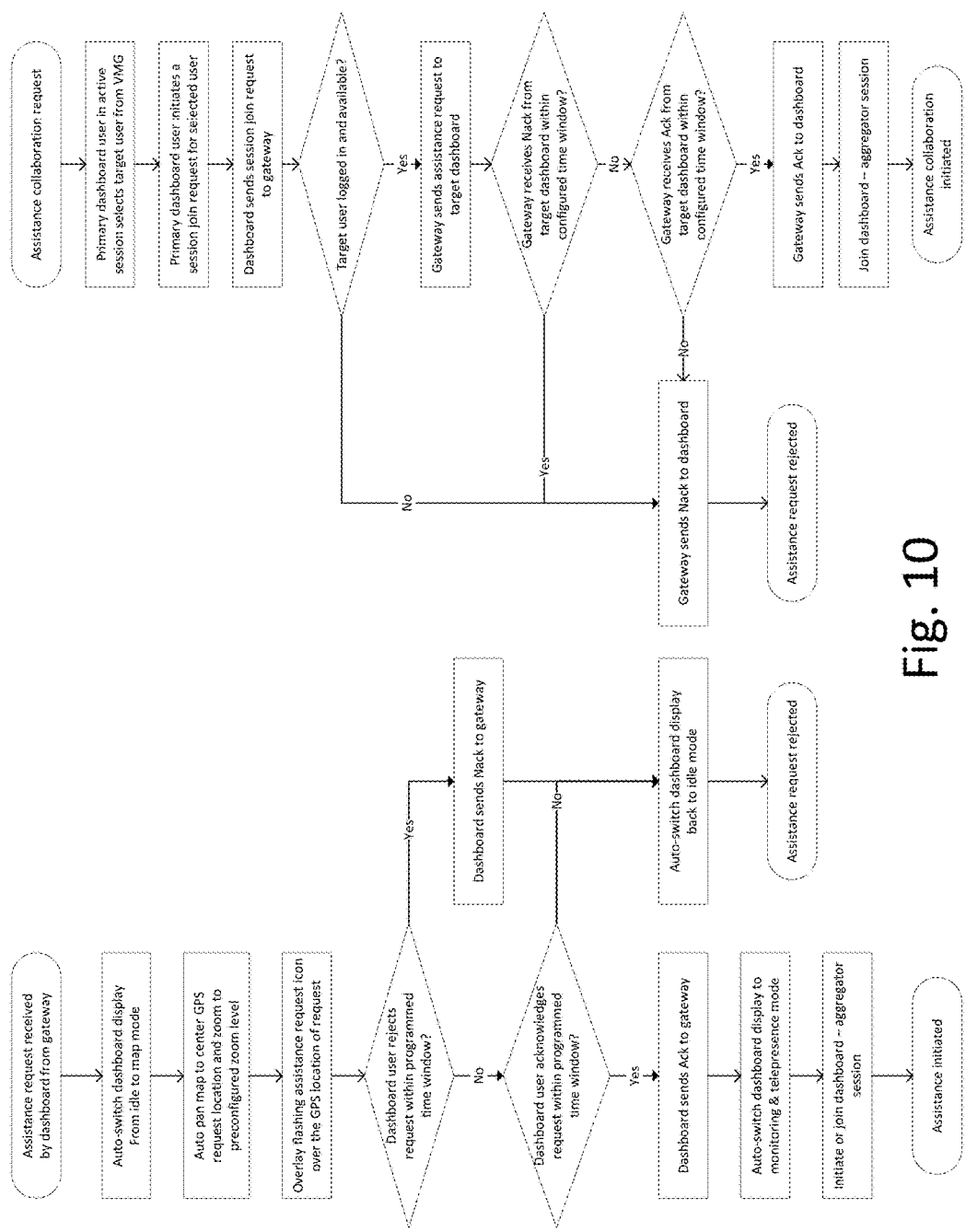
FIG. 10 illustrates typical assistance request logic and workflows for a primary dashboard and a secondary dashboard within the same session, according to the embodiments of the present invention.

FIG. 10 illustrates typical assistance request logic and workflows for a primary dashboard user and a secondary dashboard user within the same session, according to the embodiments of the present invention.

Various modifications and additions can be made to the exemplary embodiments discussed without departing from the scope of the present invention. For example, while the embodiments described above refer to the particular features, the scope of this invention also includes embodiments having different combinations of features and embodiments that do not include all of the described features. The scope of the present invention is therefore intended to embrace all such modifications, alternatives, and variations that fall within the scope of the claims, together with all the equivalents thereof.

What is claimed is:

1. A distributed telemedicine system for medical remote assistance applications, the telemedicine system comprising:
   a. one or more patient monitoring devices, the patient monitoring device comprising:
      i. one or more vital signs sensors configured for physical attachment to a patient;
      ii. a first communication system;

iii. a first processor configured to receive vital signs information from the one or more sensors, generate streaming vital signs data based on the information and transmit at least a first portion of the streaming vital signs data to an aggregator via the first communication system;
iv. a first screen configured to display a representation of at least a second portion of the streaming vital signs;

b. one or more aggregators, the aggregator comprising:
i. one or more audio and video sensors;
ii. a second communication system;
iii. a third communication system;
iv. a fourth communication system;
v. a fifth communication system;
vi. a second processor configured to receive site audio and video from the audio and video sensors and streaming vital signs from the one or more patient monitoring devices via the second communication system, transmit at least a third portion of the streaming vital signs data to a first gateway via the third communication system, transmit the site audio and video to a second gateway via the fourth communication system, and receive backchannel audio data from a third gateway via the fifth communication system;
vii. a first application executed on the second processor, the application configured to detect the presence of the first communication system and establish a communication link between the first and second communication system, detect the presence of a sixth communication system and establish a communication link between the third and sixth communication system, detect the presence of a seventh communication system and establish a communication link between the fourth and seventh communication system, detect the presence of an eighth communication system and establish a communication link between the fifth and eighth communication system;
viii. a second screen configured to display an aggregated representation of at least a fourth portion of the streaming vital signs data together with the site video and session controls;
ix. one or more first audio reproduction devices configured to reproduce the backchannel audio data received as audible sounds;

c. at least one first gateway comprising:
i. a sixth communication system;
ii. a ninth communication system;
iii. a third processor configured to receive streaming vital signs data from a plurality of aggregators over the sixth communication system and send the streaming vital signs to a plurality of dashboards over the ninth communication system;
iv. a third screen configured to display session status, statistics, and configuration controls;

d. one or more second gateways, the gateway comprising:
i. a seventh communication system;
ii. the ninth communication system;
iii. a fourth processor configured to receive site audio and video from a plurality of aggregators over the seventh communication system and send the site audio and video data to a plurality of dashboards over the ninth communication system;
iv. a fourth screen configured to display session status, statistics, and configuration controls;

e. one or more third gateways, the gateway comprising:
i. an eighth communication system;
ii. the ninth communication system;
iii. a fifth processor configured to receive backchannel audio data from a plurality of dashboards over the ninth communication system and transmit backchannel audio data to a plurality of aggregators over the eighth communication system;
iv. a fifth screen configured to display session status, statistics, and configuration controls;

f. one or more dashboards, the dashboard comprising:
i. a tenth communication system;
ii. an audio sensor;
iii. a sixth processor configured to receive site audio and video and streaming vital signs data from a gateway over the tenth communication system and to send audio backchannel data to a gateway over the tenth communication system;
iv. one or more audio reproduction devices configured to reproduce the site audio data received as audible sounds;
v. a second application executed on the sixth processor, the application configured to detect the presence of the ninth communication system and establish a communication link between the ninth and tenth communication system;
vi. a sixth screen configured to display an aggregated representation of at least a fifth portion of the streaming vital signs and clinical alarms and alerts with a representation of the site video received together with session controls;
vii. one or more second audio reproduction devices configured to reproduce the site audio data received as audible sounds.

2. The telemedicine system of claim 1, wherein the third, fourth, and sixth communication systems comprise the same systems.

3. The telemedicine system of claim 2, wherein the sixth, seventh, and eighth communication systems the same systems.

4. The telemedicine system of claim 3, wherein the first, second, and third gateways comprise the same gateways.

5. The telemedicine system of claim 4, wherein the first, second, third, fourth, and fifth portion of the streaming vital signs data comprise the same portions.

6. The telemedicine system of claim 5, wherein at least a portion of either communication system includes a fixed network over wire, fiber optic, or power line cables in either point-to-point, shared media, bus, ring, backbone, star, backhaul, ad-hoc, or mesh topology configuration.

7. The telemedicine system of claim 6, wherein at least a portion of either communication system includes a wireless network, including radio, satellite, microwave, laser, infrared, or cellular including Time Division Multiple Access (TDMA), Code Division Multiple Access (CDMA), Global System for Mobile Communications (GSM), Long-Term Evolution (LTE), Extended Long-Term Evolution (XLTE), in either point-to-point, shared media, bus, ring, backbone, star, backhaul, ad-hoc, or mesh topology configuration.

8. The telemedicine system of claim 7, wherein either of the gateways are cloud-based virtual or physical server instances.

9. The telemedicine system of claim 8, wherein either of the gateways are a server cluster system capable of redirecting, recording, or modifying communication between transmitters and receivers with manual or automatic computing resource scaling.

10. The telemedicine system of claim 9, wherein at least a portion of the data transmission over either of the communication systems uses as baseline protocols either Transmission Control Protocol/Internet Protocol (TCP/IP), User gram Protocol (UDP), Internet Control Message Protocol (ICMP), or their FastPath Stack successor.

11. The telemedicine system of claim 10, wherein at least a portion of the data transmission over either of the communication systems is secured with an encryption method consisting of the Secure Sockets Layer (SSL) protocol or Transport Layer Security (TLS).

12. The telemedicine system of claim 11, wherein at least a portion of the audio and/or video transmission over either of the communication systems uses the World Wide Web Consortium's (W3C) Web Real-Time Communication (WebRTC) protocol.

13. The telemedicine system of claim 12, wherein at least a portion of the streaming vital signs data transmission over either of the communication systems uses the Internet Engineering Task Force's (IETF) WebSocket protocol.

14. The telemedicine system of claim 13, wherein access to either of the communication systems is protected with either single or multiple factor authentication schemes consisting of a user ID/password, a digital certificate including the Public Key Infrastructure (PKI)-based X.509 certificate, a biometric reading including the image of a fingerprint, a retinal scan, or facial recognition.

15. The telemedicine system of claim 14, wherein the audio, video, and streaming vital signs data transmitted over either of the communication systems are partitioned in fixed size packets each representing a time interval configurable to any value between 20 milliseconds and 2 seconds.

16. The telemedicine system of claim 15, wherein either of the communication systems transmit new packets of either audio, video, or vital signs data at constant time intervals, programmable between 40 to 960 milliseconds.

17. The telemedicine system of claim 16, wherein either of the data packets transmitted over either of the communication systems is structured according to JavaScript Object Notation (JSON) specification.

18. The telemedicine system of claim 17, wherein either of the packets transmitted over either of the communication systems uses a compression algorithm including OPUS, iSAC, iLBC, VP8, VP9, VP10, H.264, H.265, Huffman Coding, arithmetic coding, context-free weighing (CTW), RunLength Limited (RLL), Lempel-Ziv 77 (LZ77), Lempel-Ziv 78 (LZW78), Lempel-Ziv-Storer-Symanski (LZSS), Lempel-Ziv-Markov (LZM), Lempel-Ziv-Welch (LZW), Burrows-Wheeler Transform (BZT), Brotti, Zopfli, Sequitur, Prediction by Partial Matching (PPM) including zip, gzip, pkzip, arc, rar, and may also include derived information used to detect the tampering and/or corruption of the payload including an electronic signature performed with the aid of symmetric or asymmetric key scheme, a hash, a checksum, a digital watermark, and a cryptographic timestamp.

19. The telemedicine system of claim 18, wherein the streaming vital signs include waveforms such as 3, 5, 7, or 12-lead electrocardiogram (ECG), respiration, invasive blood pressure, and temperature; trending numeric parameters such as blood oxygen saturation level (SPO2), End-Tidal CO2 (EtCO2), heart rate, respiration rate, non-invasive blood pressure, temperature, streaming ultrasound images, streaming endoscopic images, stethoscope ascultation patterns; patient monitor generated alarms including ventricular fibrillation, and patient monitor generated alerts including blood pressure lower than a preset alert limit.

20. The telemedicine system of claim 19, wherein either of the patient monitoring devices is a monitor-defibrillator.

21. The telemedicine system of claim 19, wherein either of the patient monitoring devices is a single parameter sensor with communication capabilities.

22. The telemedicine system of claim 19, wherein either of the patient monitoring devices is a multiple parameter sensor with communication capabilities.

23. The telemedicine system of claim 19, wherein the patient monitor and the aggregator are the same.

24. The telemedicine system of claim 19, wherein the aggregator, the first gateway, the second gateway, and the third gateway comprise the same component.

25. The telemedicine system of claim 19, wherein the first gateway, the second gateway, the third gateway, and the dashboard comprise the same component.

26. The telemedicine system of claim 19, wherein either of the aggregators are portable.

27. The telemedicine system of claim 19, wherein either of the aggregators are smart phones.

28. The telemedicine system of claim 19, wherein either of the dashboards are portable.

29. The telemedicine system of claim 19, wherein either of the screens are touch-enabled.

30. The telemedicine system of claim 19, wherein the first, second, and third gateways are the same and they also comprise:
   a. a first persistent memory device
   b. a third application executed on the third processor, the application configured to capture and store within the first persistent memory device a timestamped copy of all the site audio, video, backchannel audio, and streaming vital signs data passing through the gateway.

31. The telemedicine system of claim 30, wherein the gateway further comprises:
   a. a fourth application executed on the third processor, the application configured to:
      i. respond to pause, play back, rewind, and fast forward commands received over the ninth communication system;
      ii. read the timestamped site audio, video, backchannel audio, and streaming vital signs data stored in the persistent memory device;
      iii. apply a controlled time offset for each such function requested, and send it to one or more dashboards over the ninth communication system to provide the requested pause, play back, rewind, and fast forward functionality within the dashboard's fourth screen;
   and the dashboard further comprises:
   a. a fifth application executed on the fourth processor, the application configured to read user input and transmit pause, play back, rewind, and fast forward commands to the gateway's fourth application via the tenth communication system.

32. The telemedicine system of claim 30, wherein the gateway's third application is also programmed to capture and store within the first persistent memory device a timestamped copy of all the site audio, video, backchannel audio, textual chat messages, and streaming vital signs received by the gateway even if either the ninth or the tenth communication systems are inoperative, to be made available under the request and control of the dashboard by the gateway's fourth application when both the ninth and the tenth communication systems resume their operation and reconnect.

33. The telemedicine system of claim 32, wherein the aggregator also comprises:
   a. a second persistent memory device;
   b. a fifth application executed on the second processor, the application configured to capture and store a persistent, timestamped copy of all the site audio, video, and streaming vital signs data received by the aggregator when either the third, fourth, or fifth communication system is inoperative; and
      i. the aggregator's second application is also configured to send the catch-up data in a catch-up mode, until all the catch-up data is exhausted, to the one or more gateways when all of the third, fourth, and fifth communication systems resume their operation and reconnect; and
      ii. the gateway's third application is also configured to receive the timestamped catch-up data from the gateway through the sixth, seventh, and eighth communication system respectively, insert and store the catch-up, until all the catch-up data is exhausted, in its correct timestamp order within the first persistent memory device simultaneously with it storing in the same first persistent memory a timestamped copy of all the current site audio, video, backchannel audio, and streaming vital signs data passing through the gateway.

34. The telemedicine system of claim 19, wherein the first, second, and third gateways are the same and they also comprise:
   a. a sixth application executed on the third processor, the application configured to group a plurality of gateway login accounts and a plurality of dashboard login accounts into Virtual Medical Groups (VMG) and only allow the communication of site audio, video, backchannel audio, and vital signs data between the gateways and dashboards where the users logged in belong to the same VMG, and
      i. the gateway's third screen also configured to allow a system administrator to create, modify, and remove VMGs through the allocation and deallocation of individual gateway and dashboard login accounts to VMGs, in either an exclusive or a shared fashion.

35. The telemedicine system of claim 34, wherein the aggregator also comprises:
   a. a first GPS location sensor;
   b. a seventh application executed on the second processor, the application configured to:
      i. read its GPS position from its first GPS sensor;
      ii. initiate an assistance request combined with its GPS position indicating the type of expertise sought;
      iii. transmit the assistance request to one or more gateways via the fifth communication system; and
the gateway also comprises:
   a. an eighth application executed on the third processor which is programmed to:
      i. receive the assistance requests;
      ii. forward the assistance request to one or more of the dashboards whose logged in users belong to the same VMG as the user logged into the requesting gateway and according to a preprogrammed priority based on their type of expertise registered with the system; and
      iii. if the user does not confirm the assistance request within the preprogrammed time, forward the assistance request, according to a preprogrammed escalation logic and based on their type of expertise registered with the system, to another dashboard whose logged in user belongs to the same VMG as the requesting gateway's logged-in user; or
      iv. if no dashboard with a logged in user belonging to the same VMG as the requesting gateway's logged-in user exists at that time, hail the next recipient according to a programmed escalation logic and based on their type of expertise registered with the system through an external channel including a SMS message over a cellular network, an e-mail, a text-to-speech voice message over a cellular or traditional phone network
the dashboard also comprises:
   a. a ninth application executed on the fourth processor, the application programmed to:
      i. display the assistance request on a geolocation map using the GPS information embedded in the assistance request
      ii. wait for the logged in user to confirm, and
      iii. if the user is logged in and confirms the request within a programmed window of time, initiate an end-to-end audio, video, and streaming vital signs session between the dashboard and the requesting aggregator through the connecting gateway, or
      iv. if the user hailed though an external channel and logs into the dashboard, display the pending assistance request on a geolocation map using the GPS information embedded in the assistance request, and
      v. wait for the logged in user to confirm, and
      vi. if confirmed within a programmed window of time, initiate an end-to-end audio, video, and streaming vital signs session between the dashboard and the requesting aggregator through the connecting gateway.

36. The telemedicine system of claim 35, wherein the dashboard's ninth application executed on the fourth processor is also programmed to:
   a. allow a dashboard user already providing assistance to an aggregator user through an active end-to-end session to send a secondary assistance request based on second skill set which can be the same or different from their own to another nominated or generic user from the same VNG through the tenth communication system, or
   b. if not already providing assistance to a gateway user, display a pending assistance request on a geolocation map using the GPS information embedded in the original assistance request, and
   c. wait for the user to confirm, and
   d. if confirmed within a programmed window of time, initiate a secondary dashboard session with the same gateway user as the dashboard user placing the secondary assistance request, and
   e. the dashboard's fourth screen is also configured to render, when the dashboard is in such a secondary assistance mode, a replica of the primary session's streaming, waveforms, trending parameters, clinical alarms and alerts, and site video; and
   f. the dashboard's second audio reproduction device is also configured to reproduce, when the dashboard is in such a secondary assistance mode, a replica of the site audio combined with the composite backchannel audio originating from all the session's active dashboards, and
the gateway's eighth application executed on the third processor is also programmed to:
   a. receive such a secondary assistance request, and b. dispatch it to the nominated user or to the next qualified user from the same VMG and according to its programmed escalation logic.

37. The telemedicine system of claim 36, wherein the eighth application executed on the gateway's third processor is also programmed to:
   a. combine all backchannel audio originating from the primary and all secondary dashboard users providing assistance to the same gateway user, and
   b. send the combined audio backchannel forward to the aggregator and back to the primary and all secondary dashboards connected to the same gateway session.

38. The telemedicine system of claim 30, wherein:
   a. the third, fourth, and fifth communication systems are the same, and
   b. the sixth, seventh, and eighth communication systems are the same, and
   c. the first, second, and third gateways are the same, and
   d. the site audio, video, and streaming vital signs data are partitioned in packets each representing such data originating within the same 40 to 960 milliseconds time interval, and
   e. all such packets are further combined in a single composite data packet that encompasses all site audio, video, and streaming vital signs data originating within the said time interval.

39. The telemedicine system of claim 30, wherein the gateway also comprises:
   a. a tenth application executed on the third processor, the application configured to:
      i. take a snapshot of ECG data from the gateway's first persistent memory device;
      ii. perform a 12-Lead analysis through a third-party analysis module including, GE-Marquette 12SL, Glasgow 12-Lead ECG Analysis, ZOLL Inovise, Philips EASI;
      iii. generate a 12 Lead ECG analysis report, and
      iv. send such report to the dashboard via the gateway successively over the fourth, eighth, and the ninth communication systems, and
   the dashboard also comprises:
   a. an eleventh application executed on the fourth processor, the application configured to:
      i. send a 12 Lead ECG analysis request to the gateway over the tenth communication system, and
      ii. receive the 12 Lead analysis report, and
   the dashboard's fourth screen is also configured to render the said 12 Lead Analysis report.

40. The telemedicine system of claim 39 wherein:
   a. the gateway's tenth application executed on the third processor is also configured to archive the generated 12 Lead ECG analysis report into the gateway's first persistent memory device;
   b. the gateway's fourth application executed on the third processor is also programmed to:
      i. respond to a retrieval command of a previously generated 12 Lead ECG analysis report; and
      ii. send such report to the dashboard over the ninth communication system;
   c. the dashboard's eleventh application executed on the fourth processor is also configured to:
      i. send a retrieval command for a previously generated 12 Lead ECG analysis to the gateway over the tenth communication system; and
      ii. receive the said 12 Lead analysis report from the gateway over the tenth communication system; and
   d. the dashboard's fourth screen is also configured to render the previously generated 12 Lead Analysis report received from the gateway.

41. The telemedicine system of claim 40, wherein the gateway's tenth application executed on the third processor is also configured to perform, display, and archive derivative calculations, analysis, and derive alarms or alerts executed across any number of streaming vital signs, including ECG, temperature, invasive blood pressure, and respiration waveforms, trending parameters including EtCO2, SPO2, temperature, respiration rate, heart rate, non-invasive blood pressure, ultrasound and endoscopic images, auscultation waveforms, and/or including the patient monitor generated alarms and alerts.

42. The telemedicine system of claim 41, wherein the gateway's tenth application executed on the third processor is also configured to use machine learning algorithms included but not limited to, neural networks, fuzzy logic, artificial intelligence, based on previously stored streaming vital signs data received from at least a portion of all the other patients' vital signs received and stored in its first persistent memory device.

43. The telemedicine system of claim 42 wherein the gateway's tenth application executed on the third processor is also configured to use for its machine learning algorithms externally provided historical streaming vital signs data either:
   a. preloaded into the gateway's first persistent memory device; or
   b. downloaded from an external data provider over its eighth communication system; or
   c. a combination of internally stored and externally accessed such data.

44. The telemedicine system of claim 39, wherein:
   a. the gateway's tenth application executed on the third processor is also configured to archive a time stamped textual and/or voice recording annotation event into the gateway's first persistent memory device alongside the currently recorded site audio, video, and streaming vital signs data, and
   b. the gateway's fourth application executed on the third processor is also programmed to:
      i. receive a current annotation event for storage;
      ii. respond to a voice or textual retrieval command of a previously stored annotation event;
      iii. generate a search specification based on an algorithm including voice recognition, text to speech, neural networks, fuzzy logic, artificial intelligence, Boolean, binary tree;
      iv. search based on the generated search specification and its associated algorithm;
      v. locate, and send such previously stored annotation event together with all the previously stored backchannel audio, site audio, video, and streaming vital signs data in a configurable time window surrounding the time stamp of the first annotation event match to the dashboard over the ninth communication system; and
   c. the dashboard's eleventh application executed on the fourth processor is also configured to:
      i. capture a new textual or voice recorded annotation event, and
      ii. send it to the gateway over its tenth communication system;
      iii. capture a textual or voice search request for a previously stored annotation event, and iv. send it to the gateway over the tenth communication system;
v. receive the said previously stored annotation event together with all the previously stored site audio, video, and streaming vital signs data from its configurable time window from the gateway over the tenth communication system, and
d. the dashboard's fourth screen is also configured to render the received annotation event synchronized and together with all the received site audio, video, and streaming vital signs data from its configurable time window.

45. The telemedicine system of claim 44 wherein:
a. the dashboard's eleventh application executed on the fourth processor is also configured to:
i. capture a search request to be executed over the site and/or backchannel voice recorded in the gateway's first persistent data storage device, and
ii. send it to the gateway over its tenth communication system, and
iii. receive the said previously stored backchannel audio, site audio, video, and streaming vital signs data from the gateway over its tenth communication system, and
b. the gateway's fourth application executed on the third processor is also programmed to:
i. apply its generated search criteria to the site and/or backchannel voice data recorded in the gateway's first persistent data storage device, and
ii. send such previously stored backchannel audio, site audio, video, and streaming vital signs data in a configurable time window surrounding the time stamp of the first audio match to the dashboard over the ninth communication system, and
c. the dashboard's fourth screen is also configured to render the received backchannel audio, site audio, video, and streaming vital signs data from its configurable time window.

46. The telemedicine system of claim 45, wherein:
a. the gateway's fourth application executed on the third processor is also programmed to send either the first, last, next, or previous such search's match to the dashboard over the ninth communication system in response to a request received from it, and
b. the dashboard's eleventh application executed on the fourth processor is also configured to request the first, last, next, or previous such search's match.

47. The telemedicine system of claim 46, wherein:
a. the gateway also comprises a twelfth application executed on the third processor, the application configured to:
i. receive a textual or voice search request for a procedural guidance, and
ii. generate a search specification based on an algorithm including voice recognition, text to speech, neural networks, fuzzy logic, artificial intelligence, Boolean, binary tree and
iii. search based on the generated search specification and its associated algorithm, and
iv. locate and retrieve a previously stored procedural guidance including text, hypertext, annotated text, structured text, images, audio, or video, in response to a textual or voice search request received from the aggregator over the eighth communication system, and
v. send the first match of such previously stored procedural guidance to the requesting aggregator over the eighth communication system, and
b. the aggregator also comprises a thirteenth application executed on the second processor, the application configured to:
i. capture a textual or voice search request for a procedural guidance, and
ii. send it to the gateway over the fifth communication system, and
c. the aggregator's second screen is further configured to render the received procedural guidance in its appropriate representation, whether text, images, audio, or video, either as standalone or as an overlay.

48. The telemedicine system of claim 47 wherein the gateway's twelfth application executed on the third processor is also configured to search and retrieve procedural guidance data downloaded from an external data provider over its eighth communication system, or a combination of internally stored and externally accessed procedural guidance data.

49. The telemedicine system of claim 48, wherein:
a. the gateway's twelfth application executed on the third processor is also programmed to send to the aggregator either the first, last, next, or previous such search's match over the eighth communication system in response to a request received from it, and
b. the aggregator's thirteenth application executed on the second processor is also configured to request the first, last, next, or previous such search's match.

50. The telemedicine system of claim 49, wherein the gateway also comprises a portable augmented reality display including headset, goggle, retinal scanning device, and smart glass eyewear programmed to display the said procedural guidance data received from the gateway over the fifth communication system.

51. The telemedicine system of claim 50, wherein:
a. the gateway also comprises a haptic feedback device, and
b. the gateway's second screen is also configured to trigger and actuate the haptic feedback device in response to a selection of preprogrammed biological conditions detected in the streaming vital signs being displayed including heart beats, respiratory cycles, preprogrammed biological parameter limits including temperature, EtCO2, SPO2, invasive blood pressure being reached, and when patient monitor-generated alarm or alert conditions are being detected as part of the streaming vital signs being displayed.

52. The telemedicine system of claim 51, wherein:
a. the dashboard also comprises a haptic feedback device, and
b. the dashboard's fourth screen is also configured to trigger and actuate the haptic feedback device in in response to a selection of preprogrammed biological conditions detected in the streaming vital signs being displayed including heart beats, respiratory cycles, preprogrammed biological parameter limits including temperature, EtCO2, SPO2, invasive blood pressure being reached, and when patient monitor-generated alarm or alert conditions are being detected as part of the streaming vital signs being displayed.

53. The telemedicine system of claim 52 wherein the haptic feedback pattern is programmed to be unique for each group or individual type of biological conditions, alarms, or alert triggers.

54. The telemedicine system of claim 30 wherein:
a. the dashboard also comprises a video sensor, and
b. the dashboard's fourth processor is also configured to:
  i. receive streaming video from the video sensor, and
  ii. synchronize the video stream with the backchannel audio, and
  iii. transmit it as backchannel video to a gateway over the tenth communication system, and
c. the gateway's third processor is also configured to:
  i. receive backchannel video from a dashboard over the ninth communication system, and
  ii. transmit the received backchannel video to an aggregator over the eighth communication system and simultaneously to all other dashboards connected to the same active session over the ninth communication system, and
d. the dashboard's fourth processor is also configured to receive backchannel video originating from all the other dashboards connected to the same active session, and
e. the dashboard's fourth display is also configured to render the backchannel video originating from all the other session dashboards in independent sections, each identifying its originating dashboard user, and
f. the aggregator's second processor is also configured to receive backchannel video from a gateway over its fifth communication system, and
g. the aggregator's second display is also configured to render the backchannel video originating from all session dashboards in independent sections, each identifying its originating dashboard user.

55. The telemedicine system of claim 54 wherein the gateway's third application executed on the third processor is further configured to capture and store within the first persistent memory device a timestamped copy of all the backchannel video data passing through the gateway.

56. The telemedicine system of claim 30 wherein:
a. the dashboard also comprises a second GPS location sensor;
b. the dashboard's fourth processor is also configured to:
  i. read its GPS location data from its second GPS sensor, and
  ii. transmit said GPS data to a gateway over the tenth communication system;
c. the gateway's third processor is also configured to:
  i. receive GPS location data from a dashboard over the ninth communication system, and
  ii. simultaneously transmit said GPS data to all other dashboards connected to the same active session over the ninth communication system;
d. the dashboard's fourth processor is also configured to:
  i. receive GPS location data originating from all the other dashboards connected to the same active session, and
  ii. the dashboard's geolocation map is also configured to display the GPS location of all the other session dashboards as independent icons, each identifying its originating dashboard user.

57. The telemedicine system of claim 56 wherein:
a. the gateway's third processor is also configured to transmit GPS location data received from a dashboard to an aggregator over the eighth communication system;
b. the aggregator's second processor is also configured to receive GPS location data from a gateway over its fifth communication system, and
c. the aggregator's second display is also configured to display the GPS location of all session as independent icons, each identifying its originating dashboard user.

58. The telemedicine system of claim 57 wherein the gateway's third application executed on the third processor is further configured to capture and store within the first persistent memory device a timestamped copy of all the GPS location data passing through the gateway.

59. The telemedicine system of claim 58 wherein the gateway's third application executed on the third processor is further configured to export any and all of its stored audio, video, vital signs, and GPS data to an external memory device and make it available for retrieval through a Web page, a Web service, or a TCP socket interface.

60. The telemedicine system of claim 59 wherein the gateway's third application executed on the third processor is further configured to automatically purge old records of its stored audio, video, vital signs, and GPS data according to a preprogrammed record retention policy.

61. A distributed telemedicine method for allowing a plurality of medical teams assisting a plurality of patients to interact with and get assistance from a plurality of remote physicians via a plurality of audio, video, and vital signs transmissions, comprising:
a. monitoring one or more patients with patient monitoring devices, the patient monitoring device having one or more vital signs sensors configured for physical attachment to a patient, and
b. receiving vital signs information from the vital signs sensors, and
c. generating streaming vital signs data based on the information from the vital signs sensors, and
d. transmitting at least a first portion of the streaming vital signs data to an aggregator while simultaneously displaying a representation of at least a second portion of the streaming vital signs data on a first screen;
e. receiving the streaming vital signs send by one or more patient monitoring devices by an aggregator, the aggregator having one or more audio and video sensors and one or more first audio reproduction devices, and
f. transmitting at least a third portion of the streaming vital signs data from the aggregator to a first gateway, and
g. capturing site audio and video from the aggregator's sensors while transmitting the site audio and video to a second gateway, and simultaneously receiving backchannel audio from a third gateway, and
h. displaying an aggregated representation of at least a fourth portion of the streaming vital signs data together with the site video and session controls on a second screen, and
i. reproducing the backchannel audio received by the aggregator through its first audio reproduction devices;
j. receiving the site audio and video by a first gateway, and
k. maintaining session status, statistics, and configuration on the gateway via a third screen, and
l. receiving streaming vital signs data by a second gateway, and
m. sending backchannel audio to the aggregator from a third gateway, and
n. maintaining session information relating to a source aggregator connected to one or more dashboards within the gateway, and
o. sending site audio and video combined with the streaming vital signs to one or more session dashboards while simultaneously receiving backchannel audio from one or more session dashboards and transmitting the combined backchannel audio to the source aggregator;

p. receiving site audio and video and streaming vital signs by a dashboard, the dashboard having one or more audio sensors and one or more second audio reproduction devices, and q. displaying an aggregated representation of at least a fifth portion of the streaming vital signs data and clinical alarms and alerts with a representation of the site video and session controls on a fourth screen, and r. capturing audio backchannel data from the dashboard's audio sensor and sending it back to the gateway, while simultaneously reproducing the site audio as audible sounds on the dashboard's second audio reproduction devices.

62. The telemedicine method of claim 61, wherein the third, fourth, and sixth communication systems comprise the same system.

63. The telemedicine method of claim 62, wherein the sixth, seventh, and eighth communication systems comprise the same system.

64. The telemedicine method of claim 63, wherein the first, second, and third gateways comprise the same gateway.

65. The telemedicine method of claim 64, wherein the first, second, third, fourth, and fifth portion of the streaming vital signs data comprise the same portion.

66. The telemedicine method of claim 65, wherein at least a portion of either communication system includes a fixed network over wire, fiber optic, or power line cables in either point-to-point, shared media, bus, ring, backbone, star, backhaul, ad-hoc, or mesh topology configuration.

67. The telemedicine method of claim 66, wherein at least a portion of either communication system includes a wireless network, including radio, satellite, microwave, laser, infrared, or cellular including Time Division Multiple Access (TDMA), Code Division Multiple Access (CDMA), Global System for Mobile Communications (GSM), Long-Term Evolution (LTE), Extended Long-Term Evolution (XLTE), in either point-to-point, shared media, bus, ring, backbone, star, backhaul, ad-hoc, or mesh topology configuration.

68. The telemedicine method of claim 67, wherein either of the gateways are cloud-based virtual or physical server instances.

69. The telemedicine method of claim 68, wherein either of the gateways are a server cluster system capable of redirecting, recording, or modifying communication between transmitters and receivers with manual or automatic computing resource scaling.

70. The telemedicine method of claim 69, wherein at least a portion of the data transmission over either of the communication systems uses as baseline protocols either Transmission Control Protocol/Internet Protocol (TCP/IP), User gram Protocol (UDP), Internet Control Message Protocol (ICMP), or their FastPath Stack successor.

71. The telemedicine method of claim 70, wherein at least a portion of the data transmission over either of the communication systems is secured with an encryption method consisting of the Secure Sockets Layer (SSL) protocol or Transport Layer Security (TLS).

72. The telemedicine method of claim 71, wherein at least a portion of the audio and/or video transmission over either of the communication systems uses the World Wide Web Consortium's (W3C) Web Real-Time Communication (WebRTC) protocol.

73. The telemedicine method of claim 72, wherein at least a portion of the streaming vital signs data transmission over either of the communication systems uses the Internet Engineering Task Force's (IETF) WebSocket protocol.

74. The telemedicine method of claim 73, wherein access to either of the communication systems is protected with either single or multiple factor authentication schemes consisting of a user ID/password, a digital certificate including the Public Key Infrastructure (PKI)-based X.509 certificate, a biometric reading including the image of a fingerprint, a retinal scan, or facial recognition.

75. The telemedicine method of claim 74, wherein the audio, video, and streaming vital signs data transmitted over either of the communication systems are partitioned in fixed size packets each representing a time interval configurable to any value between 20 milliseconds and 2 seconds.

76. The telemedicine method of claim 75, wherein either of the communication systems transmit new packets of either audio, video, or vital signs data at constant time intervals, programmable between 40 to 960 milliseconds.

77. The telemedicine method of claim 76, wherein either of the data packets transmitted over either of the communication systems is structured according to JavaScript Object Notation (JSON) specification.

78. The telemedicine method of claim 77, wherein either of the packets transmitted over either of the communication systems uses a compression algorithm including OPUS, iSAC, iLBC, VP8, VP9, VP10, H.264, H.265, Huffman Coding, arithmetic coding, context-free weighing (CTW), RunLength Limited (RLL), Lempel-Ziv 77 (LZ77), Lempel-Ziv 78 (LZW78), Lempel-Ziv-Storer-Symanski (LZSS), Lempel-Ziv-Markov (LZM), Lempel-Ziv-Welch (LZW), Burrows-Wheeler Transform (BZT), Brotti, Zopfli, Sequitur, Prediction by Partial Matching (PPM) including zip, gzip, pkzip, arc, rar, and may also include derived information used to detect the tampering and/or corruption of the payload including an electronic signature performed with the aid of symmetric or asymmetric key scheme, a hash, a checksum, a digital watermark, and a cryptographic timestamp.

79. The telemedicine method of claim 78, wherein the streaming vital signs include waveforms including 3, 5, 7, or 12-lead electrocardiogram (ECG), respiration, invasive blood pressure, and temperature; trending numeric parameters including blood oxygen saturation level (SPO2), End-Tidal CO2 (EtCO2), heart rate, respiration rate, non-invasive blood pressure, temperature, streaming ultrasound images, streaming endoscopic images, stethoscope ascultation patterns; patient monitor generated alarms including ventricular fibrillation, and patient monitor generated alerts including blood pressure lower than a preset alert limit.

80. The telemedicine method of claim 79, wherein either of the patient monitoring devices is a monitor-defibrillator.

81. The telemedicine method of claim 79, wherein either of the patient monitoring devices is a single parameter sensor with communication capabilities.

82. The telemedicine method of claim 79, wherein either of the patient monitoring devices is a multiple parameter sensor with communication capabilities.

83. The telemedicine method of claim 79, wherein the patient monitor and the aggregator are the same.

84. The telemedicine method of claim 79, wherein the aggregator, the first gateway, the second gateway, and the third gateway comprise the same component.

85. The telemedicine method of claim 79, wherein the first gateway, the second gateway, the third gateway, and the dashboard comprise the same component.

86. The telemedicine method of claim 79, wherein either of the aggregators are portable.

87. The telemedicine method of claim 79, wherein either of the aggregators are smart phones.

88. The telemedicine method of claim 79, wherein either of the dashboards are portable.

89. The telemedicine method of claim 79, wherein either of the screens are touch-enabled.

90. The telemedicine method of claim 79, wherein the first, second, and third gateways are the same and they also capture and store a timestamped copy of all the site audio, video, backchannel audio, and streaming vital signs data passing through the gateway.

91. The telemedicine method of claim 90, wherein:
  a. the dashboard also reads user input and transmits pause, play back, rewind, and fast forward commands to the gateway, and
  b. the gateway also reads the timestamped site audio, video, backchannel audio, and streaming vital signs data stored in its first persistent memory device, and
  c. applies a controlled time offset for each such function requested, and
  d. sends it back to the requesting dashboard, and
  e. the dashboard also displays the received video on the dashboard's fourth screen, and
  f. the dashboard also renders the received audio through its second audio reproduction device.

92. The telemedicine method of claim 90, wherein the gateway also stores within the first persistent memory device a timestamped copy of all the site audio, video, backchannel audio, textual chat messages, and streaming vital signs data received by the gateway even if it loses connectivity with the dashboard, and makes it available to the dashboard under its request and control when the dashboard reconnects with the gateway.

93. The telemedicine method of claim 92, wherein:
  a. the aggregator also stores a timestamped copy of all the site audio, video, and streaming vital signs data received by the aggregator in a second persistent memory device even when it loses connectivity with the gateway, and
  b. when it reconnects with the gateway, the aggregator also sends the catch-up data to the gateway in parallel with its normal live data transmission, in a catch-up mode, until all the catch-up data is exhausted, and
  c. the gateway also inserts and stores the received catch-up data, in its correct timestamp order, on its first persistent memory device.

94. The telemedicine method of claim 79, wherein the first, second, and third gateways are the same and:
  a. the gateway groups a plurality of gateway login accounts and a plurality of dashboard login accounts into Virtual Medical Groups (VMG), and
  b. the gateway only allows the communication of site audio, video, backchannel audio, and vital signs between the gateways and dashboards where the users logged in belong to the same VMG, and
  c. the gateway allows a system administrator to create, modify, and remove VMGs through the allocation and deallocation of individual gateway and dashboard login accounts to VMGs, in either an exclusive or a shared fashion.

95. The telemedicine method of claim 94, wherein:
  a. the aggregator also reads its location position from a first GPS sensor, and
  b. initiates an assistance request combined with its GPS position indicating the type of expertise sought, and
  c. transmits the assistance request to one or more gateways;
  d. the gateway also receives the assistance requests and forwards them to one or more of the dashboards whose logged in users belong to the same VMG as the user logged into the requesting gateway and according to a preprogrammed priority based on their type of expertise registered with the system;
  e. the dashboard also displays the assistance request on a geolocation map using the GPS information embedded in the assistance request, and
  f. waits for the logged in user to confirm, and
  g. if confirmed within a programmed window of time, initiates an end-to-end audio, video, and streaming vital signs session between the dashboard and the requesting aggregator through the connecting gateway, or
  h. If the user does not confirm the assistance request within the preprogrammed time, the gateway forwards the assistance request, according to a preprogrammed escalation logic and based on their type of expertise registered with the system, to another dashboard whose logged in user belongs to the same VMG as the requesting gateway's logged in user, or
  i. If no dashboard with a logged in user belonging to the same VMG as the requesting gateway's logged in user exists at that time, the gateway hails the next recipient, according to a programmed escalation logic and based on their type of expertise registered with the system, through an external channel including a SMS message over a cellular network, an e-mail, a text-to-speech voice message over a cellular or traditional phone network and
  j. the dashboard also displays the pending assistance request on a geolocation map using the GPS information embedded in the assistance request when the user hailed though an external channel logs into the dashboard, and
  k. waits for the logged in user to confirm, and
  l. if confirmed within a programmed window of time, initiates an end-to-end audio, video, and streaming vital signs session between the dashboard and the requesting aggregator through the connecting gateway.

96. The telemedicine method of claim 95, wherein:
  a. a dashboard user providing assistance to an aggregator user through an active end-to-end session sends a secondary assistance request based on the same or different requested second skill set to another nominated or generic user from the same VNG, and
  b. the gateway receives such a secondary assistance request and dispatches it to the nominated user or to the next qualified user from the same VMG and according to its programmed escalation logic, and
  c. the dashboard also displays the secondary user's pending assistance request on a geolocation map using the GPS information embedded in the original assistance request, and
  d. waits for the secondary user to confirm, and
  e. if confirmed within a programmed window of time, initiates a secondary dashboard session with the same gateway user as the dashboard user placing the secondary assistance request, and
  f. when the dashboard is in such a secondary assistance mode, it:
    i. displays a replica of the primary session's streaming waveforms, trending parameters, clinical alarms and alerts, and site video on its fourth display, and
    ii. reproduces a replica of the site audio combined with the composite backchannel audio originating from all session dashboards on its second audio reproduction device.

97. The telemedicine method of claim 96, wherein:
a. the gateway also combines all backchannel audio originating from the primary and all secondary dashboard users providing assistance to the same gateway user, and
b. sends the combined audio backchannel forward to the aggregator and back to the primary and all secondary dashboards connected to the same gateway session.

98. The telemedicine method of claim 90, wherein the site audio, video, and streaming vital signs data are partitioned in packets each representing such data originating within the same 40 to 960 milliseconds time interval, and whereby all such packets are further combined in a single composite data packet that encompasses all site audio, video, and streaming vital signs data originating within the said time interval.

99. The telemedicine method of claim 98, wherein:
a. the dashboard also sends a 12 Lead analysis request to the gateway, and
b. the gateway also takes a snapshot of ECG data from its first persistent memory device, and
c. performs a 12-Lead analysis through a third-party analysis module including GE-Marquette 12SL, Glasgow 12-Lead ECG Analysis, ZOLL Inovise, Philips EASI and
d. generates a 12 Lead ECG analysis report, and
e. sends such report back to the dashboard, and
f. the dashboard also receives the 12 Lead analysis report, and
g. renders it on its fourth display.

100. The telemedicine method of claim 99 wherein:
a. the gateway also archives the generated 12 Lead ECG analysis report into the gateway's first persistent memory device, and
b. the dashboard also sends a retrieval command for a previously generated 12 Lead ECG analysis to the gateway, and
c. the gateway also responds to a retrieval command of a previously generated 12 Lead ECG analysis report, and
d. sends such report to the dashboard, and
e. the dashboard receives the said 12 Lead analysis report from the gateway, and
f. renders it on its fourth display.

101. The telemedicine method of claim 100, wherein the gateway also performs, displays, and archives derivative calculation, analysis, alarm, or alert executed across any number of streaming vital signs, including ECG, temperature, invasive blood pressure, and respiration waveforms, trending numerical parameters including EtCO2, SPO2, temperature, streaming ultrasound or endoscopic images, auscultation waveforms, respiration rate, heart rate, non-invasive blood pressure, and/or including patient monitor generated alarms and alerts.

102. The telemedicine method of claim 101, wherein the gateway uses machine learning algorithms including neural networks, fuzzy logic, artificial intelligence, based on previously stored streaming vital signs data received from at least a portion of all the other patients' vital signs received and stored in its first persistent memory device to improve the accuracy of at least a portion of all of its derivative calculations, analyses, alarms, or alerts.

103. The telemedicine method of claim 102 wherein the gateway uses for its machine learning algorithms externally provided historical streaming vital signs data either pre-loaded into the gateway's first persistent memory device or downloaded from an external data provider, or a combination of internally stored and externally accessed such data.

104. The telemedicine method of claim 103, wherein:
a. the dashboard also captures a new time stamped textual or voice recorded annotation event and sends it to the gateway, and
b. the gateway also receives the time stamped textual and/or voice recording annotation event, and
c. stores it into the gateway's first persistent memory device alongside the currently recorded site audio, video, and streaming vital signs data, and
d. the dashboard also captures a textual or voice search request for a previously stored annotation event, and
e. sends it to the gateway, and
f. the gateway also responds to a voice or textual retrieval command of a previously stored annotation event by generating a search specification based on an algorithm including voice recognition, text to speech, neural networks, fuzzy logic, artificial intelligence, Boolean, binary tree, searching based on the generated search specification and its associated algorithm, locating, and sending such previously stored annotation event together with all the previously stored backchannel audio, site audio, video, and streaming vital signs in a configurable time window surrounding the time stamp of the first annotation event match back to the dashboard, and
g. the dashboard also receives the said previously stored annotation event together with all the previously stored site audio, video, and streaming vital signs data from its configurable time window from the gateway, and
h. renders it on its fourth display.

105. The telemedicine method of claim 104 wherein:
a. the dashboard also captures a search request to be executed over the site and/or backchannel voice data recorded in the gateway's first persistent data storage device, and
b. sends it to the gateway, and
c. the gateway also applies its generated search criteria to the site and/or backchannel voice data recorded in the gateway's first persistent data storage device, and
d. sends such previously stored backchannel audio, site audio, video, and streaming vital signs data in a configurable time window surrounding the time stamp of the first match back to the dashboard, and
e. the dashboard receives the said backchannel audio, site audio, video, and streaming vital signs data from its configurable time window from the gateway, and
f. renders it on its fourth display.

106. The telemedicine method of claim 105, wherein:
a. the dashboard also requests the first, last, next, or previous such search's match, and
b. the gateway also sends either the first, last, next, or previous such search's match, as requested, back to the dashboard.

107. The telemedicine method of claim 106, wherein:
a. the aggregator also captures a textual or voice search request for a procedural guidance, and
b. sends it to the gateway, and
c. the gateway also responds to such a request by generating a search specification based on an algorithm including voice recognition, text to speech, neural networks, fuzzy logic, artificial intelligence, Boolean, binary tree, searching based on the generated search specification and its associated algorithm, locating and retrieving a previously stored procedural guidance including text, hypertext, annotated text, structured text, images, audio, or video, and sending the first match of such previously stored procedural guidance to the requesting aggregator, and
d. the aggregator also receives the requested data, and
e. renders the received procedural guidance in its appropriate representation, whether text, images, audio, or video, either as standalone or as an overlay.

108. The telemedicine method of claim 107 wherein the gateway also searches and retrieves procedural guidance data downloaded from an external data provider, or a combination of internally stored and externally accessed procedural guidance data.

109. The telemedicine method of claim 108, wherein:
a. the aggregator also requests the first, last, next, or previous such search's match, and
b. the gateway also locates and sends to the aggregator either the first, last, next, or previous such search's match, as requested.

110. The telemedicine method of claim 109, wherein the gateway also displays the said procedural guidance data received from the gateway on a portable augmented reality display including headset, goggle, retinal scanning device, and smart glass eyewear.

111. The telemedicine method of claim 110, wherein the gateway also triggers and actuates a built-in haptic feedback device in response to a selection of preprogrammed biological conditions detected in the streaming vital signs being displayed including heart beats, respiratory cycles, preprogrammed biological parameter limits including temperature, EtCO2, SPO2, invasive blood pressure being reached, and when patient monitor-generated alarm or alert conditions are being detected as part of the streaming vital signs being displayed.

112. The telemedicine method of claim 111, wherein the dashboard also triggers and actuates a built-in haptic feedback device in response to a selection of preprogrammed biological conditions detected in the streaming vital signs being displayed including heart beats, respiratory cycles, preprogrammed biological parameter limits including temperature, EtCO2, SPO2, invasive blood pressure being reached, and when patient monitor-generated alarm or alert conditions are being detected as part of the streaming vital signs being displayed.

113. The telemedicine method of claim 112 wherein the haptic feedback pattern is programmed to be unique for each group or individual type of biological conditions, alarms, or alert triggers.

114. The telemedicine method of claim 90 wherein:
a. the dashboard also captures streaming video data from a built-in video sensor, and
b. transmits it as backchannel video to a gateway;
c. the gateway also receives backchannel video from a dashboard, and
d. transmits the received backchannel video to an aggregator and simultaneously to all other dashboards connected to the same active session;
e. the dashboard also receives backchannel video originating from all the other dashboards connected to the same active session, and
f. renders the backchannel video originating from all the other session dashboards in independent sections on its fourth display, each identifying its originating dashboard user;
g. the aggregator also receives backchannel video from a gateway, and
h. renders the backchannel video originating from all session dashboards in independent sections on its second display, each identifying its originating dashboard user.

115. The telemedicine method of claim 114 wherein the gateway also captures and stores within the first persistent memory device a timestamped copy of all the backchannel video data passing through it.

116. The telemedicine method of claim 90 wherein:
a. the dashboard also captures GPS location data from a built-in GPS sensor, and
b. transmits it as GPS data to a gateway;
c. the gateway also receives GPS location data from a dashboard, and
d. simultaneously transmits it to all other dashboards connected to the same active session;
e. the dashboard also receives GPS location data originating from all the other dashboards connected to the same active session, and
f. displays on its geolocation map the GPS location of all the other session dashboards as independent icons, each identifying its originating dashboard user.

117. The telemedicine method of the claim 116 wherein:
a. the gateway also transmits GPS location data received from a dashboard alongside backchannel audio to an aggregator;
b. the aggregator also receives GPS location data from a gateway, and
c. displays the GPS location of all session as independent icons, each identifying its originating dashboard user, on its second display.

118. The telemedicine method of claim 117 wherein the gateway also captures and stores within its first persistent memory device a timestamped copy of all the GPS location data passing through the gateway.

119. The telemedicine method of claim 118 wherein the gateway also exports any and all of its stored audio, video, vital signs, and GPS data to an external memory device and also makes it available for retrieval through a Web page, a Web service, or a TCP socket interface.

120. The telemedicine method of claim 119 wherein the gateway is further configured to automatically purge old records of its stored audio, video, vital signs, and GPS data according to a preprogrammed record retention policy.

* * * * *